(12) United States Patent
Schmidt et al.

(10) Patent No.: US 9,748,605 B2
(45) Date of Patent: Aug. 29, 2017

(54) SULFUR-CONTAINING ADDITIVES FOR ELECTROCHEMICAL OR OPTOELECTRONIC DEVICES

(75) Inventors: Michael Schmidt, Seeheim-Jugenheim (DE); Nikolai Ignatyev, Duisburg (DE); Guenter Semrau, Kefenrod (DE); Walter Frank, Wuppertal (DE); Peter Barthen, Rheinberg (DE); Christoph Breitenstein, Muelheim (DE)

(73) Assignee: BASF SE, Ludwigshafen (DE)

( * ) Notice: Subject to any disclaimer, the term of this patent is extended or adjusted under 35 U.S.C. 154(b) by 481 days.

(21) Appl. No.: 14/239,908

(22) PCT Filed: Aug. 22, 2012

(86) PCT No.: PCT/EP2012/066292
§ 371 (c)(1),
(2), (4) Date: Feb. 20, 2014

(87) PCT Pub. No.: WO2013/026854
PCT Pub. Date: Feb. 28, 2013

(65) Prior Publication Data
US 2014/0193707 A1 Jul. 10, 2014

(30) Foreign Application Priority Data
Aug. 24, 2011 (DE) .......................... 10 2011 111 059

(51) Int. Cl.
*H01M 10/052* (2010.01)
*H01M 10/0567* (2010.01)
(Continued)

(52) U.S. Cl.
CPC ...... *H01M 10/0567* (2013.01); *C07D 207/04* (2013.01); *C07F 5/022* (2013.01);
(Continued)

(58) Field of Classification Search
CPC .................. H01M 10/052; H01M 10/0567
See application file for complete search history.

(56) References Cited

U.S. PATENT DOCUMENTS

2005/0211292 A1  9/2005  Chittibabu et al.
2011/0012048 A1*  1/2011  Zhang .................. H01G 9/2013
                                                    252/62.2
(Continued)

FOREIGN PATENT DOCUMENTS

DE  42 11 140 A1  10/1993
JP  55-157691 A  12/1980
(Continued)

OTHER PUBLICATIONS

J. F. King, et al., "Betylates. 3. Preparative Nucleophilic Substitution by Way of [2]-, [3]-, and [4]Betylates. Stiochiometric Phase Transfer and Substrate-Reagent Ion-Pair (SRIP) Reactions of Betylates" Journal of the American Chemical Society, vol. 104, XP002546399, Jan. 1, 1982, pp. 7108-7122.
(Continued)

*Primary Examiner* — Olatunji Godo
(74) *Attorney, Agent, or Firm* — Oblon, McClelland, Maier & Neustadt, L.L.P.

(57) ABSTRACT

The invention relates to sulfur-containing compounds of the formula I, to their preparation, and to their use as additives in electrochemical or electrooptical devices, more particularly in electrolytes for lithium batteries, lithium ion batteries, double layer capacitors, lithium ion capacitors, solar cells, electrochromic displays, sensors and/or biosensors.

16 Claims, 4 Drawing Sheets

Discharge resistance: x-axis: cycles  y-axis: ohms

(51) Int. Cl.
    *C07D 207/04*     (2006.01)
    *H01G 11/06*     (2013.01)
    *H01G 11/58*     (2013.01)
    *H01M 10/0525*     (2010.01)
    *C07F 5/02*     (2006.01)

(52) U.S. Cl.
    CPC .............. *H01G 11/06* (2013.01); *H01G 11/58* (2013.01); *H01M 10/0525* (2013.01); *Y02E 60/13* (2013.01); *Y02P 20/582* (2015.11)

(56) References Cited

U.S. PATENT DOCUMENTS

| | | |
|---|---|---|
| 2011/0045359 A1 | 2/2011 | Schmidt et al. |
| 2015/0236380 A1 | 8/2015 | Garsuch et al. |

FOREIGN PATENT DOCUMENTS

| | | |
|---|---|---|
| WO | WO 2005/055286 A2 | 6/2005 |
| WO | WO 2005/105815 A1 | 11/2005 |
| WO | WO 2006/017898 A1 | 2/2006 |
| WO | WO 2006/096578 A1 | 9/2006 |
| WO | WO 2009/132740 A2 | 11/2009 |

OTHER PUBLICATIONS

Kang Xu, "Nonaqueous Liquid Electrolytes for Lithium-Based Rechargeable Batteries" Chem. Rev., vol. 104, 2004, pp. 4303-4417.

Harry Distler, et al., "Die Bekämpfung des Algenwachstums in Rückkühlwerken mit neuen Mikroziden" Erdöl und Kohle, vol. 18, Issue 5, 1965, pp. 381-386 and cover page and ending page.

Xun He, et al., "New non-volatile and odorless organosulfur compounds anchored on ionic liquids. Recyclable reagents for Swern oxidation" Tetrahedron, vol. 62, 2006, pp. 3389-3394 and cover page.

N.J. Putochin, "Über die Einwirkung von Formaldehyd auf Pyrrolidin und Piperidin" Chem. Berichte,.vol. 55, 1922, pp. 2749-2753.

J. F. King, et al., "ω-Hydroxy-1-alkanesulfonyl Chlorides" Phosphorus and Sulfur, vol. 31, 1987, pp. 161-175 and cover page.

Alexandre Le Flohic, et al., "Unsaturated Sultones from Unsaturated Sulfonates: Synthesis by Ring-Closing Metathesis and Reactivity" Synlett, vol. 5, 2003, pp. 667-670 and cover page and English Abstract.

Peter J. Stang, et al., "Ethenyl(phenyl)iodonium-trifluormethansulfonat [$H_2C=CHIPh$][$OSO_2CF_3$]-Synthese und Verwendung als Vinyl-Kation-Äquivalent" Angew. Chemie, vol. 103, No. 11, 1991, pp. 1549-1550.

R. F. Hudson, et al., "Nucleophilic Reactivity. Part VII. The Mechanism of Hydrolysis of Some Unsaturated Esters of Methanesulphonic Acid" J. Chem. Soc. (B), 1966, pp. 237-240 and cover page.

Feng Gao, et al., "Synthesis and Use of Sulfonamide-, Sulfoxide-, or Sulfone-containing Aminoglycoside-CoA Bisubstrates as Mechanistic Probes for Aminoglycoside N-6'-acetyltransferase" Bioorganic & Medicinal Chemistry Letters, vol. 18, 2008, pp. 5518-5522.

International Search Report issued Nov. 12, 2012 in PCT/EP2012/066292.

International Preliminary Report on Patentability issued Nov. 25, 2013 in PCT/EP2012/066292 with Amended Claims and partial English language translation.

\* cited by examiner

Relative loading at RT: x-axis: discharge rate  y-axis: durability in %

Discharge resistance: x-axis: cycles  y-axis: ohms

Relative loading at RT: x-axis: discharge rate  y-axis: durability in %

Discharge resistance: x-axis: cycles  y-axis: ohms

Relative loading at RT: x-axis: discharge rate  y-axis: durability in %

Discharge resistance: x-axis: cycles  y-axis: ohms

Relative loading at RT: x-axis: discharge rate  y-axis: durability in %

Discharge resistance: x-axis: cycles  y-axis: ohms

SULFUR-CONTAINING ADDITIVES FOR ELECTROCHEMICAL OR OPTOELECTRONIC DEVICES

DESCRIPTION

The invention relates to sulfur-containing compounds of the formula I, to their preparation, and to their use as additives in electrochemical or electrooptical devices, more particularly in electrolytes for lithium batteries, lithium ion batteries, double layer capacitors, lithium ion capacitors, solar cells, electrochromic displays, sensors and/or biosensors.

A key component for electrochemical or optoelectronic devices is the electrolyte. It is a decisive influence on the lifetime, safety, and power of—for example—a lithium ion cell.

In recent years, the focus has lain more particularly on the development of additives for electrochemical cells, more particularly for lithium batteries and lithium ion batteries, and also double layer capacitors. Virtually every commercially employed electrolyte nowadays contains one additive at minimum.

These additives aim to improve chemical and electrochemical properties of the electrolyte. Even small amounts of additive may significantly improve the properties of the electrolyte. Accordingly, a large number of scientific publications and review articles deal with additives (see, for example, Chem. Rev. 104, 4303-4417). Additives are used, for example, in order to increase the thermal stability or conductivity of the electrolyte, to scavenge impurities in the electrolyte (e.g., water or HF), to improve the cycling stability, durability, and lifetime of an electrochemical cell, or to increase the reliability of the battery.

Used typically for these purposes are mostly organic compounds such as vinylene carbonate, propane sultone or vinyl acetate (for improving the cycling stability), biphenyl (overcharge protection), organic amines (scavenging of HF) or various sulfones (improving the thermal stability).

The main field of use for additives is the optimization of what is called the "Solid Electrolyte Interface" (SEI), i.e., the interface between electrode and electrolyte. This SEI is a significant influence on cycling stability, calendar ageing, and durability (high-current resistance) of the electrochemical or electrooptical device.

In the electrolyte of lithium ion batteries, for example, the lithium ions are present not as "bare" cations, but instead are enveloped by molecules of solvent. This so-called solvate shell multiplies the size of the small lithium ion.

In the charging of a lithium ion battery comprising a graphite anode, solvated lithium ions penetrate into the outer structures of the graphite anode. Since all solvents are electrochemically unstable under these extremely reducing conditions, they decompose, and organic lithium salts are formed. The lithium salts, whose solubility in the electrolyte is poor, deposit on the electrode and in the outer structures of the graphite, where they form the layer referred to as the SEI (see, e.g., Chem. Rev. 104, 4303-4417).

This layer, which is pervious for lithium ions but at the same time is electronically insulating, prevents direct contact between electrode and solvent. Further decomposition of the solvent is therefore prevented. Moreover, the SEI has a desolvating effect—that is, the lithium ion passes over the solvent molecules and migrates as a bare cation into the electrode. Without this effect, there would be a significant widening of the graphite layers during charging, and there would be a contraction as the cell discharged. Without a suitable SEI, this "breathing" would result, with increasing charge/discharge cycles, in the "crumbling" of the electrode and hence in a rapid end to the life of the battery.

Structure and properties of the SEI may be significantly influenced by additives. The objective is to achieve an improvement in cycling stability without giving rise to any deterioration in the internal resistance.

It was an object of the present invention, therefore, to develop new additives for electrolytes that react more quickly and more targetedly with charged surfaces and thus positively influence the formation of the SEI for electrochemical devices, for example.

The object is achieved in accordance with the invention by the sulfur-containing compounds of the formula I as described below.

The invention accordingly first provides compounds of the formula I (I)

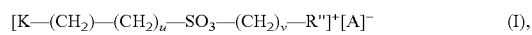

where
u is 0, 1, 2, 3, 4, 5, 6 or 7 and where at least one $CH_2$ group of the $—(CH_2)_u$-alkylene chain with u=2, 3, 4, 5, 6 or 7 may be replaced by O or may contain at least one double bond,
v is 0, 1, 2, 3 or 4,
—$SO_3$— denotes

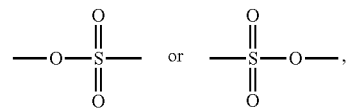

R" independently at each occurrence is a straight-chain or branched alkyl group having 1 to 20 C atoms, and may be unfluorinated, partly fluorinated or fully fluorinated, or is a straight-chain or branched alkenyl group having 2 to 20 C atoms and one or more double bonds, a straight-chain or branched alkynyl group having 2 to 20 C atoms and one or more triple bonds, or an aryl group having 6 to 12 C atoms, which group may be singly or multiply substituted by F, Cl and/or a straight-chain or branched, partly fluorinated or fully fluorinated alkyl group having 1 to 8 C atoms,
K is a cation selected from the group
$R_3N^+$—*, $R_3P^+$—*,

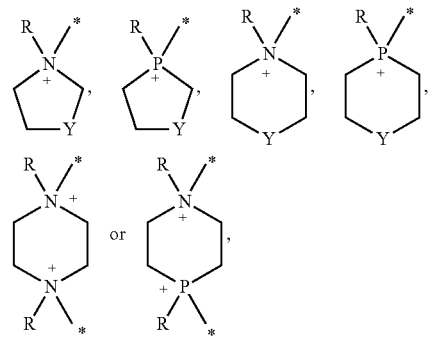

where
R independently at each occurrence is methyl, ethyl, n-propyl, isopropyl, n-butyl, sec-butyl or tert-butyl, it being possible for at least one $CH_2$ group, not directly joined to N or P, in the stated radicals R to be replaced by O, —* denotes the bond from K to the (CH$_2$) group in formula (II),
Y is CH$_2$, O, S or NR', and
R' is methyl, ethyl, n-propyl, isopropyl, n-butyl, sec-butyl or tert-butyl,
A is an anion selected from the group
[F$_z$B(C$_m$F$_{2m+1}$)$_{4-z}$]$^-$,
[F$_y$P(C$_m$F$_{2m+1}$)$_{6-y}$]$^-$,
[(C$_m$F$_{2m-1}$)$_2$P(O)O]$^-$,
[C$_m$F$_{2m+1}$P(O)O$_2$]$^{2-}$,
[O—C(O)—C$_m$F$_{2m+1}$]$^-$,
[O—S(O)$_2$—C$_m$F$_{2m+1}$]$^-$,
[N(C(O)—C$_m$F$_{2m+1}$)$_2$]$^-$,
[N(S(O)$_2$—C$_m$F$_{2m+1}$)$_2$]$^-$,
[N(C(O)—C$_m$F$_{2m+1}$)(S(O)$_2$—C$_m$F$_{2m+1}$)]$^-$,
[N(C(O)—C$_m$F$_{2m+1}$)(C(O)F)]$^-$,
[N(S(O)$_2$—C$_m$F$_{2m+1}$)(S(O)$_2$F)]$^-$,
[N(S(O)$_2$F)$_2$]$^-$,
[C(C(O)—C$_m$F$_{2m+1}$)$_3$]$^-$,
[C(S(O)$_2$—C$_m$F$_{2m+1}$)$_3$]$^-$, where
m is 1, 2, 3, 4, 5, 6, 7 or 8, it being possible partly for CF$_2$ groups in the stated anions to be replaced by O, S(O)$_2$, NR or CH$_2$,
z is 1, 2, 3 or 4,
y is 1, 2, 3, 4, 5 or 6,
X is B or Al,
R$^1$ and R$^2$ in each case independently of one another are F, Cl, Br, I, a straight-chain or branched perfluoroalkyl group having 1 to 20 C atoms, a straight-chain or branched alkoxy group having 1 to 20 C atoms, which may be unfluorinated, partly fluorinated or fully fluorinated, or —O—C(O)-alkyl, where alkyl is a straight-chain or branched alkyl group having 1 to 20 C atoms, and may be unfluorinated, partly fluorinated or perfluorinated,
and where independently at each occurrence is a bidentate radical which derives from a 1,2- or 1,3-diol, from a 1,2- or 1,3-dicarboxylic acid or from a 1,2- or 1,3-hydroxycarboxylic acid, by the entering of pairs of adjacent OH groups in the compound in question into one bond each to the central atom X, accompanied by formal elimination of two H atoms, and with the electroneutrality of the corresponding salt of the formula (I) being observed.

At potentials between about 2.5 V and 0.9 V against Li/Li$^+$, the compounds of the formula (I) according to the invention, as described above, form a passivating outer layer on the negative electrode, this layer being the SEI, as described above.

One surprising and outstanding property of these compounds of the formula (I) is that, when used as additives in electrolytes, they do not in general lead to an increase in the internal resistance of the electrochemical cell, like vinylene carbonate or propane sultone, for example.

Since the compounds of the formula (I) are salts, they are in general nonvolatile and do not possess any measurable vapor pressure. This is a further advantage over the organic additives hitherto employed, such as propane sultone, for example.

Similar compounds to the compounds of the formula (I) are described in H. Distler and E.-H. Pommer, Erdöl and Kohle, 1965, 18(5), 381-386. The quaternary ammonium salts of the taurine esters described are water-soluble microcidal compounds, more particularly for controlling algae. The counterion of these quaternary ammonium salts is methylsulfate, as for example in the compound TAS, also known under the brand name Sepacid®, i.e., the tetramethylammonium salt of taurin phenylester or else, synonymously, phenyloxysulfonylethyl trimethylammoniomethylsulfate.

DE 4211140 describes similar phosphonium salts and their use as brighteners for aqueous-acidic electronickelization baths; examples are benzyl triphenylphosphonioacetate chloride, 3-(triphenylphosphonio)propyl methyl ketone chloride, 4-(triphenylphosphonio)butyroyl chloride, methyl 4-(triphenylphosphonio)acetoacetate chloride, ethyl 5-(triphenylphosphonio)valerate bromide or triphenylphosphonioallyl chloride. Quaternary phosphonium salts of sulfonic esters with chloride or bromide as counterion are not described.

Xun He and Tak Hang Chan, Tetrahedron, 2006, 62, 3389-3394 describe nonvolatile, low-odor organosulfur compounds, anchored to ionic liquids, as recyclable reagents for the Swern oxidation, examples being the following compounds n=1, 2, 5; x=1,2

WO 2005/055286 describes zwitterionic compounds of the formula

R$_2$ = O$^-$, ⁻N—CH$_2$—R$_3$, ⁻N—(CO)—R$_3$, ⁻N—SO$_2$—R$_3$, where R$_1^+$ is a heterocyclic cation, an ammonium cation, a guanidinium cation or a phosphonium cation, A is a spacer and R$_3$ is H, alkyl, cycloalkyl, heterocyclyl, alkenyl, alkynyl or aryl, for use in a solar cell as a constituent of charge transport layers. Representatively, the following compounds are described:

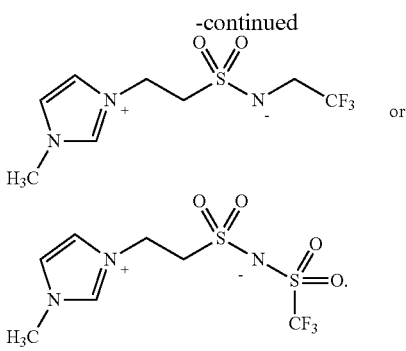

WO 2006/017898 describes zwitterionic additives for electrochemical devices, with the general structure cation-spacer-anion. Representative compounds for these zwitterions, i.e., for compounds which carry both a positive charge and a negative charge in one molecule, are the compounds N-methyl-N-(n-butansulfonate)pyrrolidinium

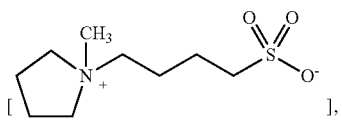

N-methyl-N-(n-propanesulfonate)pyrrolidinium or 1-butyl-imidazolium-3-(n-butanesulfonate)

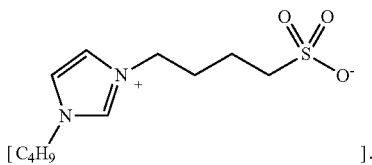

A straight-chain or branched alkyl group having 1 to 20 C atoms is for example methyl, ethyl, isopropyl, propyl, butyl, sec-butyl or tert-butyl, and also pentyl, 1-, 2- or 3-methylbutyl, 1,1-, 1,2- or 2,2-dimethylpropyl, 1-ethylpropyl, hexyl, heptyl, octyl, nonyl, decyl, undecyl, dodecyl, tridecyl, tetradecyl, pentadecyl, hexadecyl, heptadecyl, octadecyl, nonadecyl or eicosyl, which may optionally also be partly fluorinated or fully fluorinated (synonymous with perfluorinated). The expression "perfluorinated" indicates that all of the H atoms in the indicated alkyl group are substituted by F atoms. The expression "partly fluorinated" indicates that at least one H atom in the indicated alkyl group is substituted by an F atom. Examples of partly fluorinated or perfluorinated alkyl groups are difluoromethyl, trifluoromethyl, pentafluoroethyl, heptafluoropropyl or nonafluorobutyl.

A straight-chain or branched alkenyl group having 2 to 20 C atoms, in which there may also be two or more double bonds present is, for example, allyl, 2- or 3-butenyl, isobutenyl, sec-butenyl, and also 4-pentenyl, isopentenyl, hexenyl, heptenyl, octenyl, —C$_9$H$_{17}$, —C$_{10}$H$_{19}$ to —C$_{20}$H$_{39}$; preferably allyl, 2- or 3-butenyl, isobutenyl, sec-butenyl, and more preferably 4-pentenyl, isopentenyl or hexenyl.

A straight-chain or branched alkynyl group having 2 to 20 C atoms, in which there may also be two or more triple bonds present, is for example ethynyl, 1- or 2-propynyl, 2- or 3-butynyl, and also 4-pentynyl, 3-pentynyl, hexynyl, heptynyl, octynyl, —C$_9$H$_{15}$, —C$_{10}$H$_{17}$ to —C$_{20}$H$_{37}$, preferably ethynyl, 1- or 2-propynyl, 2- or 3-butynyl, 4-pentynyl, 3-pentynyl or hexynyl.

A straight-chain or branched alkoxy group having 1 to 20 C atoms is for example methoxy, ethoxy, isopropoxy, propoxy, butoxy, sec-butoxy or tert-butoxy, and also pentoxy, 1-, 2- or 3-methylbutoxy, 1,1-, 1,2- or 2,2-dimethylpropoxy, 1-ethylpropoxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy or eicosyloxy, which may be unfluorinated, partly fluorinated or fully fluorinated. The expression "partly fluorinated" indicates that at least one H atom in the indicated alkoxy group is substituted by an F atom. The expression "fully fluorinated" indicates that all of the H atoms in the indicated alkoxy group are substituted by F atoms.

An aryl group having 6 to 12 C atoms is for example phenyl, naphthyl or phenanthryl, which may be singly or multiply substituted by F, Cl and/or a straight-chain or branched, partly fluorinated or fully fluorinated alkyl group having 1 to 8 C atoms; preferably phenyl which may be substituted by F, Cl and/or a straight-chain or branched, partly fluorinated or fully fluorinated alkyl group having 1 to 8 C atoms; examples are o-, m- or p-methylphenyl, o-, m- or p-ethylphenyl, o-, m- or p-propylphenyl, o-, m- or p-(iso-propyl)phenyl, o-, m- or p-(tert-butyl)phenyl, o-, m-, p-(trifluoromethyl)phenyl, o-, m-, p-(pentafluoroethyl)phenyl, o-, m-, p-(nonafluorobutyl)phenyl, o-, m- or p-fluorophenyl, o-, m- or p-chlorophenyl, 2,3-, 2,4-, 2,5-, 2,6-, 3,4- or 3,5-bis(trifluoromethyl)phenyl, 2,3-, 2,4-, 2,5-, 2,6-, 3,4- or 3,5-bis(pentafluoroethyl)-phenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 5-fluoro-2-trifluoromethylphenyl, 3,4,5-trifluorophenyl or 2,4,5-trifluorophenyl. With particular preference the aryl group having 6 to 12 C atoms is phenyl, which may be singly or multiply substituted by F and/or a straight-chain or branched, partly fluorinated or perfluorinated alkyl group having 1 to 8 C atoms.

The representation

denotes, independently at each occurrence, a bidentate radical which derives from a 1,2- or 1,3-diol, from a 1,2- or 1,3-dicarboxylic acid or from a 1,2- or 1,3-hydroxycarboxylic acid, by the entering in each case of two adjacent OH groups in the compound in question into one bond in each case with the central atom X, with the formal elimination of two H atoms.

Suitable 1,2- or 1,3-diols for generating the bidentate radical as described above are not only aliphatic but also aromatic, examples being 1,2-dihydroxybenzene (catechol, pyrocatechol), propane-1,2-diol, butane-1,2-diol, propane-1,3-diol, butane-1,3-diol, cyclohexyl-trans-1,2-diol or naphthalene-2,3-diol, which may optionally be singly or multiply substituted by F and/or at least one straight-chain or branched, unfluorinated, partly fluorinated or perfluorinated alkyl group having 1 to 4 C atoms. An example of 1,2- or 1,3-diols having such substitution is 1,1,2,2-tetra(trifluoromethyl)-1,2-ethanediol.

Suitable 1,2- or 1,3-dicarboxylic acids for generating the bidentate radical as described above are not only aliphatic but also aromatic, examples being oxalic acid, malonic acid (propane-1,3-dicarboxylic acid), phthalic acid or isophthalic acid, which may optionally be singly or multiply substituted by F and/or at least one straight-chain or branched, unfluorinated, partly fluorinated or perfluorinated alkyl group having 1 to 4 C atoms.

Suitable 1,2- or 1,3-hydroxycarboxylic acids for generating the bidentate radical as described above are not only aliphatic but also aromatic, examples being salicylic acid, tetrahydrosalicylic acid, malic acid and 2-hydroxyacetic acid, which may optionally be singly or multiply substituted by F and/or at least one straight-chain or branched, unfluorinated, partly fluorinated or perfluorinated alkyl group having 1 to 4 C atoms. An example of 1,2- or 1,3-hydroxycarboxylic acids having such substitution is 2,2-bis(trifluoromethyl)-2-hydroxy-acetic acid.

The variable u is 0, 1, 2, 3, 4, 5, 6 or 7; preferably u stands for 1, 2 or 3.

At least one $CH_2$ group in the $—(CH_2)_u$-alkylene chain with u=2, 3, 4, 5, 6 or 7 may be replaced by O or may contain at least one double bond. Preferably, the $—(CH_2)_u$-alkylene chain is unsubstituted and u has one of the definitions indicated above or indicated as being preferred.

The variable v is 0, 1, 2, 3 or 4; preferably v stands for 0.

Preferably, $—SO_3—$ stands for

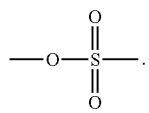

In the compounds of the formula I, R" is preferably, independently at each occurrence, a straight-chain or branched alkyl group having 1 to 20 C atoms, and may be unfluorinated, partly fluorinated or fully fluorinated, or is a straight-chain or branched alkenyl group having 2 to 4 C atoms and one or more double bonds, or is a straight-chain or branched alkynyl group having 2 to 4 C atoms and one or more triple bonds, examples being methyl, ethyl, trifluoromethyl, pentafluoroethyl, n-propyl, n-butyl, n-hexyl, n-octyl, ethenyl, ethynyl, allyl or prop-1-yn-yl.

More preferably R" independently at each occurrence is a straight-chain or branched alkyl group having 1 to 8 C atoms, and may be fluorinated, partly fluorinated or fully fluorinated. Very preferably, R" is methyl.

The variable Y in the formulae for the cations K, as described above, is $CH_2$, O, S or NR', where R' is methyl, ethyl, n-propyl, isopropyl, n-butyl, sec-butyl or tert-butyl; more preferably Y is $CH_2$.

The substituent R in the formulae for the cations K, as described above, is preferably methyl, ethyl, n-propyl or n-butyl, more preferably methyl.

In the compounds of the formula I, K is preferably the cation

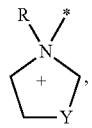

where Y and R have one of the above-indicated definitions, and very preferably it is the pyrrolidinium cation

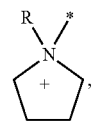

where R has one of the above-stated definitions.

The variable m in the formulae of the anions A, as described above, is preferably 1, 2, 3, 4, 5, 6, 7 or 8, more preferably 2, 3 or 4, very preferably 2 or 4.

The variable y in the formulae of the anions A, as described above, is 1, 2, 3, 4, 5 or 6, preferably 3, 4 or 5, more preferably 3 or 5, very preferably 3.

The variable z in the formulae of the anions A, as described above, is 1, 2, 3 or 4, preferably 1, 2 or 3, very preferably 3.

The variable X in the formulae of the anions A, as described above, is B or Al, preferably B.

In the compounds of the formula I, A is preferably an anion selected from the group
$[F_zB(C_mF_{2m+1})_{4-z}]^-$,
$[F_yP(C_mF_{2m+1})_{6-y}]^-$,
$[O—C(O)—C_mF_{2m+1}]^-$,
$[O—S(O)_2—C_mF_{2m+1}]^-$,
$[N(S(O)_2—C_mF_{2m+1})_2]^-$,
$[N(S(O)_2F)_2]^-$,

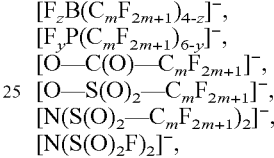

where
m is 1, 2, 3, 4, 5, 6, 7 or 8,
z is 1, 2 or 3,
y is 3, 4, 5 or 6,
X is B,
$R^1$ and $R^2$ in each case independently of one another are F, a straight-chain or branched perfluoroalkyl group having 1 to 4 C atoms, a straight-chain or branched alkoxy group having 1 to 4 C atoms or $—O—C(O)$-alkyl, where alkyl is a straight-chain or branched alkyl group having 1 to 20 C atoms, and may be unfluorinated, partly fluorinated or perfluorinated, and where

independently at each occurrence is a bidentate radical which derives from a 1,2- or 1,3-diol, from a 1,2- or 1,3-dicarboxylic acid or from a 1,2- or 1,3-hydroxycarboxylic acid, by the entering of pairs of adjacent OH groups in the compound in question into one bond each to the central atom X, accompanied by formal elimination of two H atoms.

In the compounds of the formula I, A is more preferably an anion selected from the group
$[F_yP(C_mF_{2m+1})_{6-y}]^-$,

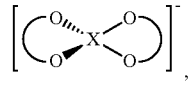

where
m is 2, 3 or 4,
y is 3, 4 or 5,
X is B,
and where

independently at each occurrence is a bidentate radical which derives from a 1,2- or 1,3-diol, from a 1,2- or 1,3-dicarboxylic acid or from a 1,2- or 1,3-hydroxycarboxylic acid, by the entering of pairs of adjacent OH groups in the compound in question into one bond each to the central atom X, accompanied by formal elimination of two H atoms.

Preferred anions of the formula $[F_zB(C_mF_{2m+1})_{4-z}]^-$ are the anions $[F_3B(CF_3)]^-$ or $[F_3B(C_2F_5)]^-$.

Preferred anions of the formula $[F_yP(C_mF_{2m+1})_{6-y}]^-$ are the anions $[PF_6]^-$, $[F_3P(C_2F_5)_3]^-$, $[F_3P(C_3F_7)_3]^-$, $[F_3P(C_4F_9)_3]^-$, $[F_4P(C_2F_5)_2]^-$, $[F_4P(C_3F_7)_2]^-$, $[F_4P(C_4F_9)_2]^-$, $[F_5P(C_2F_5)]^-$, $[F_5P(C_3F_7)]^-$ or $[F_5P(C_4F_9)]^-$, more preferably $[PF_6]^-$, $[F_3P(C_2F_5)_3]^-$, $[F_3P(C_3F_7)_3]^-$, $[F_3P(C_4F_9)_3]^-$, $[F_5P(C_2F_5)]^-$, $[F_5P(C_3F_7)]^-$ or $[F_5P(C_4F_9)]^-$, very preferably $[F_3P(C_2F_5)_3]^-$ and $[F_5P(C_2F_5)]^-$.

Preferred anions of the formula $[(C_mF_{2m+1})_2P(O)O]^-$ are the anions $[(C_2F_5)_2P(O)O]^-$, $[(C_3F_7)_2P(O)O]^-$ or $[(C_4F_9)_2P(O)O]^-$.

Preferred anions of the formula $[C_mF_{2m+1}P(O)O_2]^{2-}$ are the anions $[C_2F_5P(O)O_2]^{2-}$, $[C_3F_7P(O)O_2]^{2-}$ or $[C_4F_9P(O)O_2]^{2-}$.

Preferred anions of the formula $[O-C(O)C_mF_{2m+1}]^-$ are the anions $[O-C(O)CF_3]^-$, $[O-C(O)C_2F_5]^-$ or $[O-C(O)C_4F_9]^-$, more preferably $[O-C(O)CF_3]^-$.

Preferred anions of the formula $[O-S(O)_2C_mF_{2m+1}]^-$ are the anions $[O-S(O)_2CF_3]^-$ or $[O-S(O)_2C_2F_5]^-$, more preferably $[O-S(O)_2CF_3]^-$.

Preferred anions of the formula $[N(C(O)C_mF_{2m+1})_2]^-$ are the anions $[N(C(O)C_2F_5)_2]^-$ or $[N(C(O)(CF_3)_2]^-$.

Preferred anions of the formula $[N(S(O)_2C_mF_{2m+1})_2]^-$ are the anions $[N(S(O)_2CF_3)_2]^-$, $[N(S(O)_2C_2F_5)_2]^-$, $[N(S(O)_2C_3F_7)_2]^-$, $[N(S(O)_2CF_3)(S(O)_2C_2F_5)]^-$ or $[N(S(O)_2C_4F_9)_2]^-$, more preferably $[N(S(O)_2CF_3)_2]^-$.

Preferred anions of the formula $[N(C(O)C_mF_{2m+1})(S(O)_2C_mF_{2m+1})]^-$ are the anions $[N(C(O)CF_3)(S(O)_2CF_3)]^-$, $[N(C(O)C_2F_5)(S(O)_2CF_3)]^-$ or $[N(C(O)CF_3)(S(O)_2-C_4F_9)]^-$.

Preferred anions of the formula $[N(C(O)C_mF_{2m+1})(C(O)F)]^-$ are the anions $[N(C(O)CF_3)(C(O)F)]^-$, $[N(C(O)C_2F_5)(C(O)F)]^-$ or $[N(C(O)C_3F_7)(C(O)F)]^-$.

Preferred anions of the formula $[N(S(O)_2C_mF_{2m+1})(S(O)_2F)]^-$ are the anions $[N(S(O)_2CF_3)(S(O)_2F)]^-$, $[N(S(O)_2C_2F_5)(S(O)_2F)]^-$ or $[N(S(O)_2C_4F_9)(S(O)_2F)]^-$.

Preferred anions of the formula $[C(C(O)C_mF_{2m+1})_3]^-$ are the anions $[C(C(O)CF_3)_3]^-$, $[C(C(O)C_2F_5)_3]^-$ or $[C(C(O)C_3F_7)_3]^-$.

Preferred anions of the formula $[C(S(O)_2C_mF_{2m+1})_3]^-$ are the anions $[C(S(O)_2CF_3)_3]^-$, $[C(S(O)_2C_2F_5)_3]^-$ or $[C(S(O)_2C_4F_9)_3]^-$.

Preferred anions of the formula

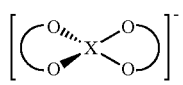

are the anions bis(catecholato)borate, in which both bidentate radicals are based on 1,2-dihydroxybenzene, bis(oxalato)borate, in which both bidentate radicals are based on oxalic acid, bis(malonato)borate, in which both bidentate radicals are based on malonic acid, malonatooxalatoborate, where one bidentate radical is based on malonic acid and one bidentate radical is based on oxalic acid, naphtholatooxalatoborate, where one bidentate radical is based on naphthalene-2,3-diol and one bidentate radical is based on oxalic acid, bis(naphtholato)borate, in which both bidentate radicals are based on naphthalene-2,3-diol, or bis(salicylato)borate, in which both bidentate radicals are based on salicylic acid; very preferably bis(oxalato)borate, abbreviated BOB.

Preferred anions of the formula

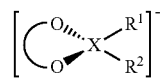

are the anions difluorooxalatoborate, di-trifluoroacetatooxalatoborate, difluorodi(trifluoromethyl)glyconatoborate, in which the bidentate radical is based on 2,2-bis(trifluoromethyl)-2-hydroxyacetic acid, difluoroperfluoropinakolatoborate, in which the bidentate radical is based on 1,1,2,2-tetra(trifluoromethyl)-1,2-ethanediol, trifluoromethylmethoxyoxalatoborate, pentafluoroethylmethoxyoxalatoborate, trifluoromethylmethoxycatecholatoborate, pentafluoroethylmethoxycatecholatoborate, trifluoromethylmethoxymalonatoborate, pentafluoroethylmethoxymalonatoborate, pentafluoroethylmethoxynaphtholatoborate or fluoropentafluoroethyloxalatoborate, more preferably difluorooxalatoborate.

Particularly preferred compounds of the formula I are the compounds

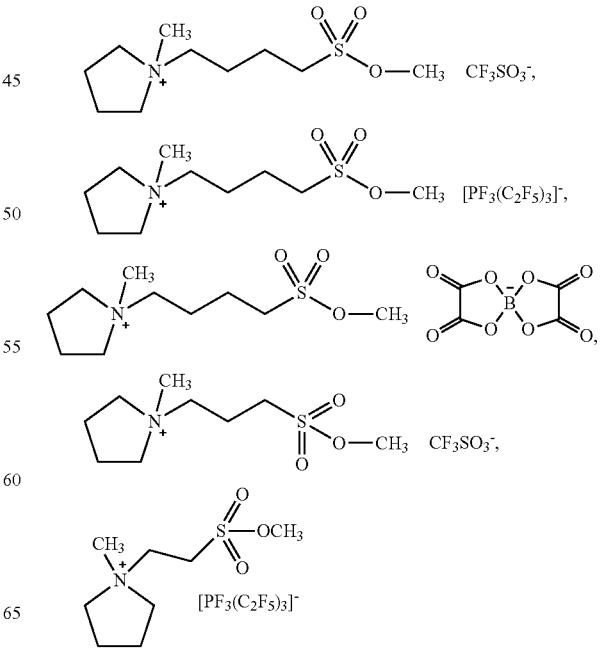

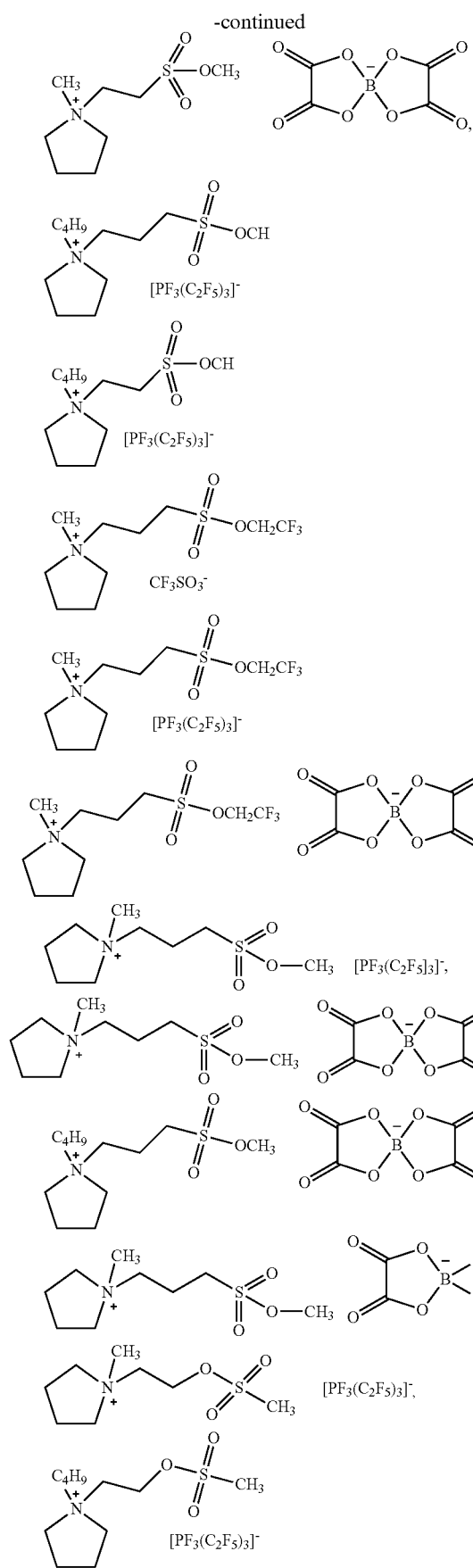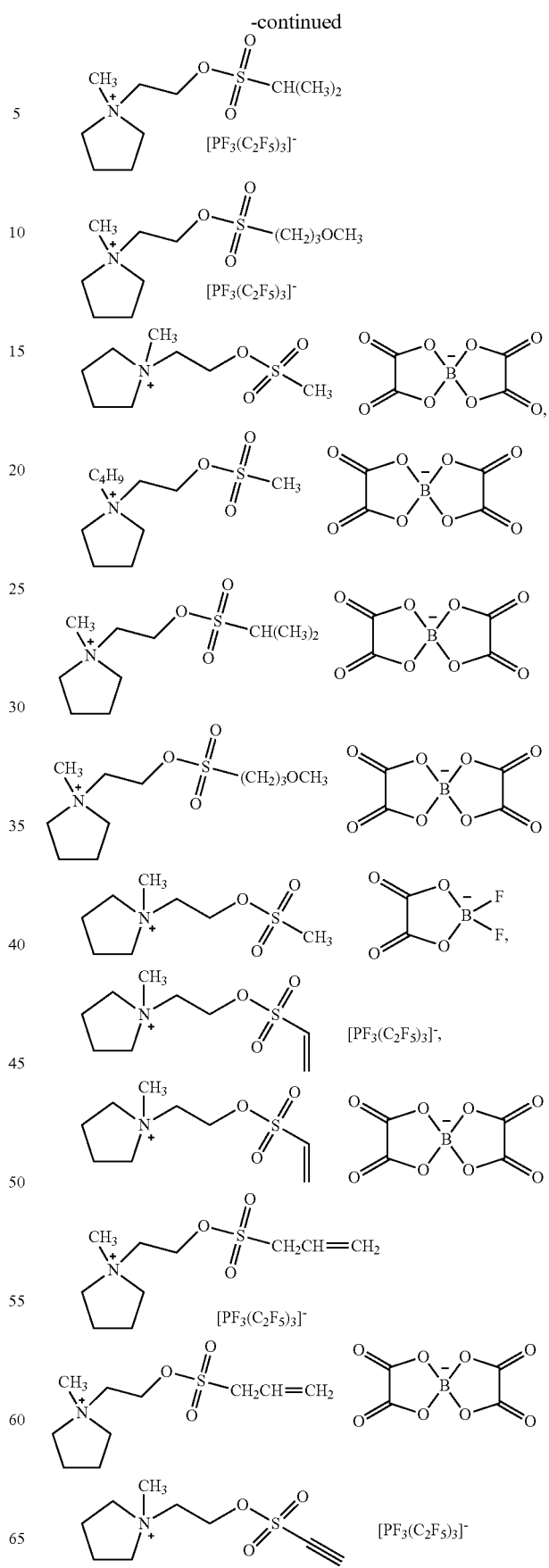

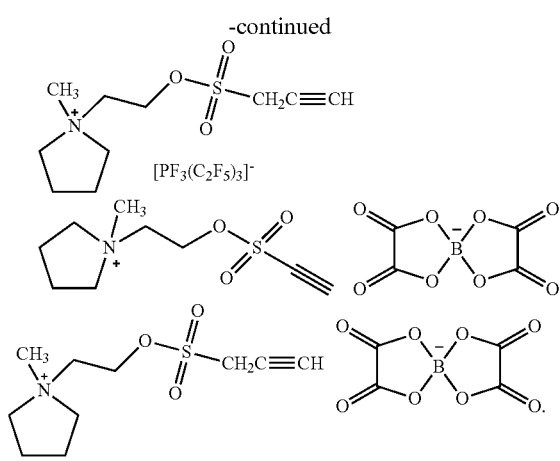

To the skilled person it is self-evident that in the compounds of the invention it is possible for substituents such as C, H, N, O, Cl and F, for example, to be replaced by the corresponding isotopes.

The compounds of the formula I as described above are generally synthesized starting from the appropriate corresponding amines or phosphines.

The multistage syntheses which are described below may take place in individual steps, with the intermediate compounds indicated correspondingly being isolated and purified, or successively, by merely adapting the further reaction conditions accordingly.

The process steps can be carried out in the air, preferably in a dry atmosphere, as for example under dry air, nitrogen or argon.

The invention accordingly further provides a process for preparing compounds of the formula I, as described above or as described as being preferred, where $SO_3$ corresponds to the substructure

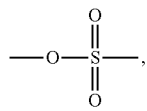

wherein a compound of the formula (II)

K-1        (II), where K-1 is selected from the group $R_3N$, $R_3P$,

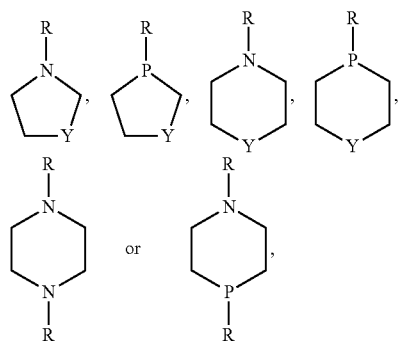

where
R independently at each occurrence is methyl, ethyl, n-propyl, isopropyl, n-butyl, sec-butyl or tert-butyl, and at least one $CH_2$ group, not joined to N or P, in the stated radicals R may be replaced by O, Y is $CH_2$, O, S or NR' and
R' is methyl, ethyl, n-propyl, isopropyl, n-butyl, sec-butyl or tert-butyl,
is first reacted with a compound of the formula (III), Hal-$(CH_2)$—$(CH_2)_u$—OH        (III), where u is 1, 2, 3, 4, 5, 6 or 7, and at least one $CH_2$ group, not attached to the oxygen, in the —$(CH_2)_u$-alkylene chain with u=3, 4, 5, 6 or 7 may be replaced by O or may contain at least one double bond, and Hal is Cl, Br or I,
and the resultant intermediate compound of the formula (IV)

[K—$(CH_2)$—$(CH_2)_u$—OH]$^+$[Hal]$^-$        (IV), where K, u and Hal have one of the above-stated definitions, is reacted with a compound of the formula (V)

R"—$(CH_2)_v$—$SO_2$-L        (V), where v and R" have an above-stated definition and L is a leaving group selected from a straight-chain or branched alkoxy group having 1 to 3 C atoms, Cl or F, preferably Cl or F, with acid catalysis in the case of the alkoxy group as leaving group, or in the presence of a base in the case of Cl or F as leaving group, and the resulting compound of the formula (VI)

[K—$(CH_2)$—$(CH_2)_u$—$SO_3$—$(CH_2)_v$—R"]$^+$[Hal]$^-$        (VI), in which K, u, v, R" and Hal have one of the above-stated definitions,
is reacted in a metathesis reaction with a compound of the formula (VII),

[Kt]$^+$[A]$^-$        (VII), where [Kt]$^+$ is an alkali metal cation or H$^+$, and [A]$^-$ has a definition described for the anions of the formula I.

Not only the compounds of the formula II but also the compounds of the formula III, as described above, are generally available commercially or can be synthesized by known methods belonging to the standard.

For the synthesis of compounds of the formula (I), as described above or as described as being preferred, where $SO_3$ corresponds to the substructure

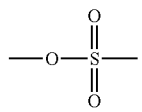

and in which u is 0, the compound N-oxymethylpyrrolidine of the formula (IIIa)

can be utilized for the further reaction in the synthesis pathway described above. The compound of the formula (IIIa) can be prepared by methods known from the literature, as described for example in N. J. Putochin, Chem. Berichte, 55, 1922, pp. 2749-2753.

The reaction of the compounds of the formula II with compounds of the formula III, as described above, takes place in general at reaction temperatures between 10° C. and 200° C., preferably between 20° C. and 100° C. In general no solvent is used.

The intermediate compounds of the formula (IV)

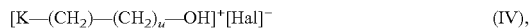
[K—(CH$_2$)—(CH$_2$)$_u$—OH]$^+$[Hal]$^-$  (IV), where K, u, and Hal have one of the above-stated definitions, are obtained generally by extraction or precipitation from the reaction mixture. Purification by conventional techniques, such as recrystallization, for example, is possible. Preference is given to carrying out further reaction without further purification of the compounds.

The reaction of the compounds of the formula (IV), as described above, with compounds of the formula (V)

R''—(CH$_2$)$_v$—SO$_2$-L  (V), where v and R'' have an above-stated definition and L is a leaving group selected from a straight-chain or branched alkoxy group having 1 to 3 C atoms, Cl or F, preferably Cl or F, corresponds to a conventional transesterification or substitution reaction, the reaction conditions for which are known to the person skilled in the art of organic synthesis.

If the leaving group L in the compound of the formula V is an alkoxy group, as described above, then the reaction takes place with acid catalysis, in the presence for example of sulfuric acid, toluenesulfonic acid, methanesulfonic or ethanesulfonic acid, Nafion®, Amberlite® or Amberlyst® in acidic form.

If the leaving group L in the compound of the formula V is Cl or F, then the reaction takes place in the presence of a base, examples being inorganic bases such as KOH, NaOH, Na$_2$CO$_3$ or NaHCO$_3$, or organic bases such as triethylamine, diisopropylethylamine or pyridine.

This substitution reaction takes place preferably in the presence of an organic solvent. The addition of the compound of the formula V is made at temperatures between −10° C. and room temperature. In order to complete the reaction, it may be advisable to carry out heating at reflux in certain cases.

In the case of the transesterification with substances of formula V, as described, in which the leaving group L is an alkoxy group, preferably methoxy group, the customary time of heating is in the order of magnitude of hours, with distillative removal in order to remove the resultant alcohol (methanol).

The intermediate compound (VI)

[K—(CH$_2$)—(CH$_2$)$_u$—SO$_3$—(CH$_2$)$_v$—R'']$^+$[Hal]$^-$  (VI), in which K, u, v, R'', and Hal have one of the above-stated definitions,
this compound being obtained from the substitution reaction, is reacted in a metathesis reaction with a compound of the formula (VII),

[Kt]$^+$[A]$^-$  (VII), where [Kt]$^+$ is an alkali metal cation or H$^+$, and [A]$^-$ has a definition described for the anions of the formula (I) or a definition described as being preferred, to form compounds of the formula (I) in which SO$_3$ corresponds to the substructure

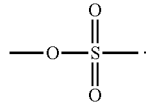

The metathesis reaction is carried out preferably in water, with suitable temperatures being 10°-100° C., preferably 15°-60° C., more preferably room temperature.

Alternatively, however, the reaction can also be carried out in organic solvents at temperatures between 10° and 100° C. Suitable solvents here are acetonitrile, acetone, 1,4-dioxane, dichloromethane, dimethoxyethane or an alcohol, such as methanol, ethanol or isopropanol, for example.

It is preferred to use sodium salts or potassium salts of the compounds of the formula (VII).

The invention further provides a process for preparing compounds of the formula (I), as described above or as described as being preferred, where SO$_3$ corresponds to the substructure

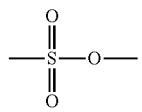

and u is 2, 3, 4 or 5, wherein a compound of the formula (II)

K-1  (II), where K-1 is selected from the group R$_3$N, R$_3$P,

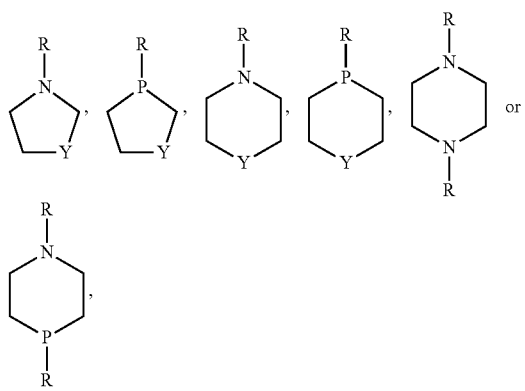

where
R independently at each occurrence is methyl, ethyl, n-propyl, isopropyl, n-butyl, sec-butyl or tert-butyl, and at least one CH$_2$ group, not joined to N or P, in the stated radicals R may be replaced by O,
Y is CH$_2$, O, S or NR', and
R' is methyl, ethyl, n-propyl, isopropyl, n-butyl, sec-butyl or tert-butyl,
is first reacted with a compound of the formula (VIII)

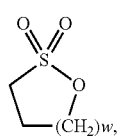

VIII where w is 1, 2, 3 or 4,
to give the intermediate compound of formula (IX)

[K—(CH$_2$)—(CH$_2$)$_u$—SO$_3^-$]  (IX), where K and u have an above-indicated definition, and subsequently the intermediate compound of the formula (IX) is reacted with an alkylating agent of the formula (X)

where v and R" have a definition indicated above or indicated as being preferred and L* is $CF_3-S(O)_2O$, $C_4F_9-S(O)_2O$, $(C_2F_5)_2P(O)O$, $(C_4F_9)_2P(O)O$, $(alkyl)_2O^+$, alkyl-S$(O)_2O$, alkyl-O—S$(O)_2O$, I or Br, with alkyl independently at each occurrence being a straight-chain or branched alkyl group having 1 to 4 C atoms,
and the resulting compound of the formula (XI)

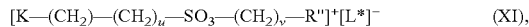

where K, u, v, R" and L* have an above-stated definition, is reacted optionally with a compound of the formula (VII),

where $[Kt]^+$ is an alkali metal cation or $H^+$, and $[A]^-$ has a definition described above for compounds of the formula I, if the anion $[L*]^-$ does not already correspond to a definition of the anion $[A]^-$.

Sultones of the formula (VIII)

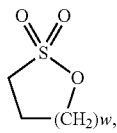

where w is 1, 2, 3 or 4, are available commercially or can be prepared by known processes, as described, for example, by J. F. King et al. in Phosphorus and Sulfur and the Related Elements, 13 (1987), pp. 161-175.

The —(CH$_2$)-cycloalkylene chain in the compound VIII may also comprise at least one double bond (A. L. Flohic et al. in Synlett, 5 (2003), pp. 667-670), but according to common general knowledge not on the C atoms which enter into a direct bond with the heteroatoms S and O.

The reaction of the commercially available compounds of the formula II, as described above, with the sultones of the formula VIII takes place without solvent or in an organic solvent, preferably in an organic solvent as for example in toluene, acetonitrile, dioxane, acetone, monoglyme, diglyme or in mixtures of acetonitrile with dialkyl ether, more preferably in toluene. The reaction takes place at temperatures between −10° C. and room temperature. In order to complete the reaction, it may be advisable to carry out heating at reflux in certain cases.

The intermediate compound of the formula (IX)

where K and u have one of the above-stated definitions, this compound being obtained from this process step, is reacted with an alkylating agent of the formula (X)

where v and R" have an above-stated definition and L* is $CF_3—S(O)_2O$, $C_4F_9—S(O)_2O$, $(C_2F_5)_2P(O)O$, $(C_4F_9)_2P(O)O$, $(alkyl)_2O^+$, alkyl-S$(O)_2O$, alkyl-O—S$(O)_2O$, I or Br, where alkyl independently at each occurrence is a straight-chain or branched alkyl group having 1 to 4 C atoms.

Alkylating agents of the formula X are available commercially or can be prepared by known processes, as for example $CF_3SO_2O—CH=CH_2$ (P. J. Stang and J. Ullmann, Angew. Chem., 103 (1991), pp. 1549-1550) or $CH_3SO_2O—CH_2CH=CH_2$ (R. F. Hudson and R. J. Withey, J. Chem. Soc. (B), 1966, pp. 237-240).

The alkylation may be carried out without solvent, in which case temperatures of 0°-150° C., preferably 0°-80° C., more preferably room temperature, are suitable.

Alternatively, however, the reaction also takes place in the presence of an organic solvent, as for example acetonitrile, propionitrile, benzonitrile, dialkyl ethers, dichloromethane, monoglyme, diglyme, more preferably in acetonitrile.

The reaction temperature is between 0° C. and 150° C., preferably between 0° C. and 80° C. It is particularly preferred to carry out reaction at room temperature.

The compounds of the formula (XI) that result from this alkylation,

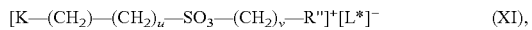

where K, u, v, R", and L* have an above-stated definition, may already represent a compound of the formula I, depending on the choice of the leaving group L*, or else, in the conventional metathesis reaction, the desired anion is introduced as a replacement, by carrying out reaction with a compound of the formula VII,

where $[Kt]^+$ is an alkali metal cation or $H^+$, and $[A]^-$ has an above-stated definition. With regard to the metathesis reaction, the observations which apply are the same as those described above.

Alternatively, the intermediate compound of the formula IX may first be reacted with an acid $[H]^+[A]^-$, where A has an above-indicated definition, and in a further step may be alkylated directly to a compound of the formula I with a diazocompound of the formula $N_2—(CH_2)_v—R"$, where v and R" have an above-indicated definition.

The invention further provides a process for preparing compounds of the formula I, as described above or as described as being preferred, where $SO_3$ corresponds to the substructure

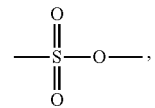

wherein a compound of the formula (II)

where K-1 is selected from the group $R_3N$, $R_3P$,

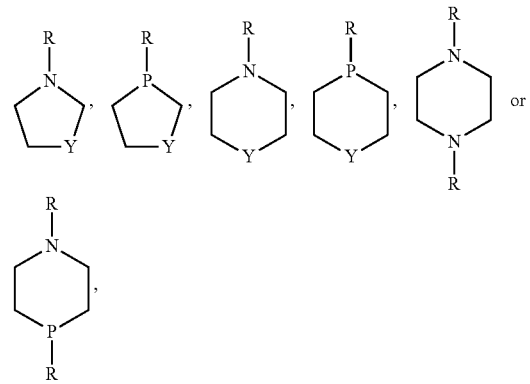

where
R independently at each occurrence is methyl, ethyl, n-propyl, isopropyl, n-butyl, sec-butyl or tert-butyl, and individual $CH_2$ groups, not joined to N or P may be replaced by O, Y is $CH_2$, O, S or NR', and
R' is methyl, ethyl, n-propyl, isopropyl, n-butyl, sec-butyl or tert-butyl,
is first reacted with a compound of the formula (XII), $$Hal\text{-}(CH_2)\text{—}(CH_2)_u\text{-}Hal \qquad (XII)$$

where u is 1, 2, 3, 4, 5, 6 or 7, and at least one $CH_2$ group, not attached to Hal, in the $—(CH_2)_u$-alkylene chain with u=2, 3, 4, 5, 6 or 7 may be replaced by O or may contain at least one double bond, and Hal is Cl, Br or I,
and the resultant intermediate compound of the formula (XIII)

$$[K\text{—}(CH_2)\text{—}(CH_2)_u\text{-}Hal]^+[Hal]^- \qquad (XIII)$$

where K, u and Hal have one of the above-stated definitions, is reacted with an alkali metal sulfite or ammonium sulfite, to give an intermediate compound of the formula IX $$[K\text{—}(CH_2)\text{—}(CH_2)_u\text{—}SO_3^-] \qquad (IX)$$

where K and u have one of the above-indicated definitions, and subsequently with an alkylating agent of the formula (X), $$L^*\text{-}(CH_2)_v\text{—}R'' \qquad (X)$$

where v and R'' have an above-indicated definition and $L^*$ is $CF_3—S(O)_2O$, $C_4F_9—S(O)_2O$, $(C_2F_5)_2P(O)O$, $(C_4F_9)_2P(O)O$, $(alkyl)_2O^+$, $alkyl\text{-}S(O)_2O$, $alkyl\text{-}O—S(O)_2O$, I or Br, with alkyl independently at each occurrence being a straight-chain or branched alkyl group having 1 to 4 C atoms.

Alternatively, a compound of the formula (II), as described above, may be alkylated first with $Hal\text{-}(CH_2)—(CH_2)_u—S(O)_2ONa$ of the formula (XIIa) (Hal is preferably Br or I and u has one of the above-stated definitions) to give an intermediate compound of the formula (IX), as described above, and reacted further with an alkylating agent of the formula (X), as described above. The preparation method for the compounds of the formula (XIIa) (u=0 and 1) is described at Feng Gao et al. in Bioorganic & Medicinal Chemistry Letters 18 (2008), pp. 5518-5522.

The compounds resulting from alkylation reaction, of the formula (XI), $$[K\text{—}(CH_2)\text{—}(CH_2)_u\text{—}SO_3\text{—}(CH_2)_v\text{—}R'']^+[L^*]^- \qquad (XI)$$

where K, u, v, R'', and $L^*$ have an above-stated definition, may already represent a compound of the formula I, depending on the choice of the leaving group $L^*$, or, in the conventional metathesis reaction, the desired anion is introduced by replacement, by reaction with a compound of the formula VII, $$[Kt]^+[A]^- \qquad (VII)$$

where $[Kt]^+$ is an alkali metal cation or $H^+$, and $[A]^-$ has an above-stated definition. With regard to the metathesis reaction, the observations described above apply.

Compounds of the formula (XII), as described above, $$Hal\text{-}(CH_2)\text{—}(CH_2)_u\text{-}Hal \qquad (XII)$$

are available commercially, where u is 0, 1, 2, 3, 4, 5, 6 or 7 and where at least one $CH_2$ group, not attached to Hal, in the $—(CH_2)_u$-alkylene chain with u=2, 3, 4, 5, 6 or 7 may be replaced by O or may contain at least one double bond, or can be prepared from the commercially available compounds of the formula $HO—(CH_2)—(CH_2)_u—OH$, where u is 1, 2, 3, 4, 5, 6 or 7 and where at least one $CH_2$ group, not attached to the oxygen, in the $—(CH_2)_u$-alkylene chain with u=3, 4, 5, 6 or 7 may be replaced by O or may contain at least one double bond. The reaction conditions of such substitutions are well known to a person skilled in the art of organic synthesis.

The resultant intermediate compound of the formula (XIII)

$$[K\text{—}(CH_2)\text{—}(CH_2)_u\text{-}Hal]^+[Hal]^- \qquad (XIII),$$

where K, u, and Hal have one of the above-stated definitions, is reacted with an alkali metal sulfite or ammonium sulfite and subsequently with a compound of the formula (X).

$$L^*\text{-}(CH_2)_v\text{—}R'' \qquad (X), \text{ as described above.}$$

The reaction conditions for such reactions with compounds of the formula (X) and the subsequent metathesis reaction have been described above and also apply correspondingly in this process.

The invention additionally provides an electrolyte comprising at least one compound of the formula (I), as described above or as described as being preferred.

Viewed chemically, an electrolyte is any substance which comprises free ions and as a result is electrically conductive. The most typical electrolyte is an ionic solution, although molten electrolytes and solid electrolytes are likewise possible.

An electrolyte of the invention or a corresponding electrolyte formulation is therefore an electrically conductive medium, primarily due to the presence of at least one substance which is present in a dissolved and/or molten state, i.e., an electrical conductivity supported by movement of ionic species.

The compounds of the formula I, as described above or as described as being preferred, take on the function of an additive in the electrolyte.

For use in lithium batteries, lithium ion batteries or lithium capacitors, the compounds of the formula I, as described above, take on the function of an additive which is especially positive in its effect on the generation of the SEI.

For use in solar cells, electrochromatic devices, sensors or biosensors, the compounds of the formula I, as described above, take on the function of an additive.

Accordingly, when the compounds of the formula I are used as an additive in the electrolytes of the invention, the typical concentration is between 0.05 and 10 percent by weight, preferably between 0.05% and 5%, based on the total weight of the electrolyte.

For the purposes of the present invention, the molarity relates to the concentration at 25° C.

The invention therefore further provides for the use of compounds of the formula (I), as described above, as additives in electrolytes.

The compounds of the formula (I), according to the invention, as described above, are used preferably in lithium batteries or lithium ion batteries or are used preferably in electrolytes which are suitable for these electrochemical devices.

Therefore, in addition to the compounds of the formula (I), as described above or as described as being preferred, the electrolyte of the invention comprises a conductive salt, preferably selected from a lithium salt and/or a tetraalkylammonium salt, the alkyl groups in each case independently denoting an alkyl group having 1 to 4 C atoms.

In one preferred embodiment, in the context of the electrolyte being used in lithium batteries or lithium ion batteries and in lithium ion capacitors, the conductive salt is a conductive lithium salt such as $LiPF_6$, $LiBF_4$, $LiN(SO_2F)_2$, $LiN(SO_2CF_3)_2$, $LiN(SO_2C_2F_5)_2$, $LiF_5P(C_2F_5)$, $LiF_5P(C_3F_7)$, $LiF_5P(C_4F_9)$, $LiF_3P(C_2F_5)_3$, $LiF_3P(C_4F_9)_3$, $LiB(C_2O_4)_2$ or $LiF_2B(C_2O_4)_2$.

In one preferred embodiment, when the electrolyte is used in double layer capacitors or supercapacitors, the conductive salt is a tetraalkylammonium salt from the group consisting of $[N(C_2H_5)_4]BF_4$, $[N(C_2H_5)_4]PF_6$, $[N(C_2H_5)_3(CH_3)]BF_4$, $[N(C_2H_5)_3(CH_3)]PF_6$, $[N(C_2H_5)_4][N(SO_2CF_3)_2]$, $[N(C_2H_5)_3(CH_3)][N(SO_2CF_3)_2]$, $[N(C_2H_5)_4][PF_3(C_2F_5)_3]$, $[N(C_2H_5)_3(CH_3)][PF_3(C_2F_5)_3]$, $[N(C_2H_5)_4][PF_4(C_2F_5)_2]$, $[N(C_2H_5)_3(CH_3)][PF_4(C_2F_5)_2]$, $[N(C_2H_5)_4][PF_5(C_2F_5)]$ and $[N(C_2H_5)_3(CH_3)][PF_5(C_2F_5)]$.

Preference is given to using 0.45 to 2 molar solutions, more preferably 1 molar solution, of the conductive lithium salt in an aprotic solvent or solvent mixture.

The electrolytes of the invention preferably comprise an aprotic solvent or solvent mixture, and also, optionally, one or more further additives. They can be used in combination with further conductive salts and/or adjuvants, as part of a polymer electrolyte or phase transfer medium.

The aprotic solvent of the electrolyte consists preferably of organic, open-chain or cyclic carbonates, carboxylic esters, nitriles, silanes or sulfonic esters, or of a mixture thereof. Nitriles, more particularly acetonitrile, are used as solvents preferably in double layer capacitors.

Preferred open-chain or cyclic carbonates are diethyl carbonate, dimethyl carbonate, ethyl methyl carbonate, ethylene carbonate or propylene carbonate.

Preferred carboxylic acid esters are ethyl acetate or methyl propionate.

Preferred nitriles are adiponitrile, valeronitrile, and acetonitrile, with acetonitrile being more preferred.

The organic solvent is preferably present in the electrolyte at 5 to 90 percent by weight, preferably at 40 to 90 percent by weight, the percent by weight figure being based on the overall electrolyte.

Further additives may be selected, for example, from the known additives vinylene carbonate, propane sultone, vinyl acetate, biphenyl, cyclohexylbenzene, organic amines, examples being trialkylamines, dialkylphenylamines or N-silylated amines, such as trimethylsilylimidazole as an example of an N-silylated cyclic amine, or various sulfones, as for example diphenyl sulphone, and the alkyl groups in the aforementioned amines may independently at each occurrence be a straight-chain or branched alkyl group having 1 to 20 C atoms.

In one preferred embodiment, the electrolyte comprises not only the additives of the formula I according to the invention, as described above, but also the additives of the stated group vinylene carbonate, propane sultone, vinyl acetate, biphenyl, cyclohexylbenzene, organic amines, N-silylated amines or sulfones, and the alkyl groups in the aforementioned amines may independently at each occurrence be a straight-chain or branched alkyl group having 1 to 20 C atoms.

Another class of additives which may be included are additives which bring about gelling for electrolytes known as gel electrolytes, these being electrolytes which take on a "quasi-solid" state. They have structural properties of solid electrolytes, but retain conductive properties like liquid electrolytes.

Gel additives of these kinds may be selected from inorganic particulate materials, such as $SiO_2$, $TiO_2$ or $Al_2O_3$, for example. The electrolytes of the invention may comprise such gel additives at 0.01 to 20 percent by weight, based on the overall electrolyte, preferably at 1 to 10 percent by weight.

When a solvent is present in the electrolyte of the invention there may also be a polymer included, the polymer being polyvinylidene fluoride, polyvinylidene-hexafluoropropylene copolymers, polyvinylidene-hexafluoropropylene-chlorotrifluoroethylene copolymers, Nafion, polyethylene oxide, polymethyl methacrylate, polyacrylonitrile, polypropylene, polystyrene, polybutadiene, polyethylene glycol, polyvinylpyrrolidone, polyaniline, polypyrrole and/or polythiophene. These polymers are added to the electrolytes in order to convert liquid electrolytes into quasi-solid or solid electrolytes and thus to improve solvent retention, especially during ageing.

The electrolytes of the invention are prepared by methods which are known to the person skilled in the field of the production of electrolytes, generally by dissolving the conductive salt in the corresponding solvent mixture and adding the additives of the formula I according to the invention, as described above.

The invention further provides an electrochemical or electrooptical device comprising at least one compound of the formula I, as described above or as described as being preferred.

The device may preferably be a lithium battery, a lithium ion battery, a double layer capacitor, a lithium ion capacitor, a solar cell, an electrochemical display, a sensor or a biosensor.

The solar cell is preferably a dye solar cell.

The invention further provides for the use of a compound of the formula I, as described above or as described as being preferred, in electrochemical or electrooptical devices, as described above.

A lithium battery is a battery in which a lithium metal electrode is used as the negative electrode.

A lithium ion battery uses as its negative electrode materials into which lithium ions can be introduced and removed reversibly. Examples thereof are graphite, silicon or silicon-carbon composites, tin oxides or lithium titanium oxides.

The general construction of such electrochemical and electrooptical devices is known and is familiar to the person skilled in this art—for batteries, for example, in Linden's Handbook of Batteries (ISBN 978-0-07-162421-3).

For example, the anode consists of carbon/graphite, the cathode of a lithium metal oxide or lithium phosphate, and the separator of polypropylene/polyethylene or of ceramic sheet.

Even without further statements, it is assumed that a skilled person is able to utilize the above description in its widest extent. Consequently, the preferred embodiments and examples are to be interpreted merely as a descriptive enclosure which in no way has any limiting effect at all.

The compounds synthesized are characterized by NMR spectroscopy. The NMR samples are subjected to measurement in 5 mm NMR tubes at 25° C. in a Bruker Avance III spectrometer, equipped with a 9.3980 T cryomagnet. The $^1H$ and $^{19}F$ NMR spectra are measured using a 5 mm combined $^1H/^{19}F$ measurement head which operates at 400.17 and 376.54 MHz. The $^{13}C$ NMR spectra are obtained by using a 5 mm broadband inverse measuring head at 100.62 MHz. The reference in the case of the $^1H$ NMR spectra is tetramethylsilane (TMS), using the chemical shifts of the solvents $CHCl_3$ (7.23 ppm) and $CH_3CN$ (1.96 ppm). Similar comments apply in respect of the $^{13}$C NMR spectra: CHCl$_3$ (77.24 ppm) and CH$_3$CN (118.70 ppm).

EXAMPLES

Example 1. Synthesis of 3-(1-methylpyrrolidinium-1-yl)propane-1-sulfonate

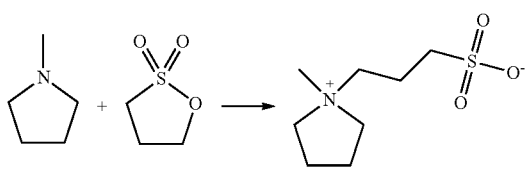

23.8 g (195 mmol) of 1,3-propane sultone in 50 ml of toluene are admixed slowly dropwise with 16.8 g (197 mmol) of methylpyrrolidine, with cooling in an ice bath. The precipitate is isolated by filtration, washed twice with toluene, and dried under reduced pressure (10$^{-3}$ hPa). This gives 37.1 g of 3-(1-methylpyrrolidinium-1-yl)-propane-1-sulfonate in the form of a hygroscopic, colorless solid. The yield is 92%.

$^1$H NMR (solvent: D$_2$O), δ (ppm): 3.98 (m, 6H); 3.55 (s, 3H); 3.42 (t, J=7.2 Hz, 2H); 2.74 (m, 6H).

$^{13}$C{$^1$H} NMR (solvent: D$_2$O), δ (ppm): 64.5 s; 62.4 s; 48.1 s; 47.5 s; 21.3 s; 19.3 s.

Example 2. Synthesis of 1-(3-(methoxysulfonyl) propyl)-1-methylpyrrolidinium tris(pentafluoroethyl) trifluorophosphate

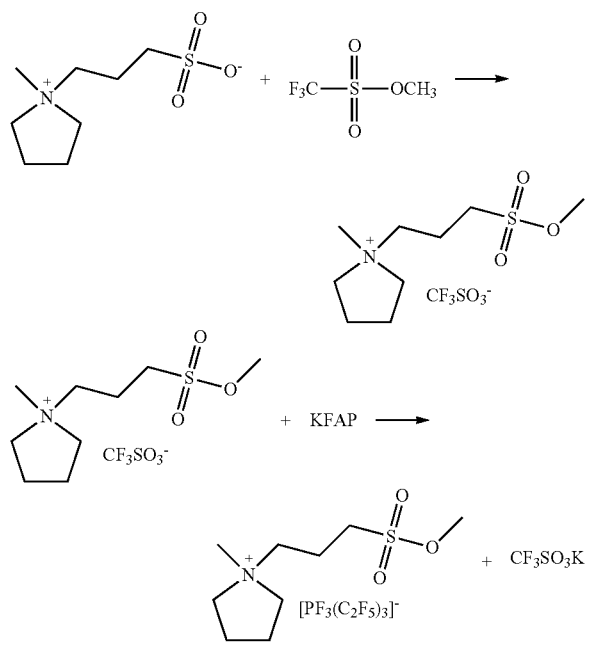

6.3 g (30.3 mmol) of 3-(1-methylpyrrolidinium-1-yl)propane-1-sulfonate are suspended in 10 ml of acetonitrile, and 5.6 g (34.0 mmol) of methyl triflate are added. The solid dissolves completely in an exothermic reaction, and the reaction mixture is stirred at room temperature for three hours. On addition of 14.7 g (30.3 mmol) of potassium tris(pentafluoroethyl)trifluorophosphate (KFAP) in 50 ml of ice-cold water, a coarse precipitate is formed. The solid is isolated, washed with four times 40 ml of water, and dried in a desiccator. This gives 19.2 g of 1-(3-(methoxysulfonyl) propyl)-1-methylpyrrolidinium tris(pentafluoroethyl)trifluorophosphate in the form of a pale yellow solid. The yield is 95%.

$^1$H NMR (solvent: CD$_3$CN), δ (ppm): 3.91 (s, 3H); 3.44 (m, 4H); 3.36 (m, 2H); 3.24 (t, J=7.4 Hz, 2H); 2.97 (s, 3H); 2.25 (m, 2H); 2.19 (m, 4H).

$^{13}$C{$^1$H} NMR (cation) (solvent: CD$_3$CN), δ (ppm): 64.7; 61.6; 56.7; 48.2; 45.2; 21.2; 18.5.

Elemental analysis; calculated (found), %: C, 27.00 (27.22), H, 3.02 (3.02), N, 2.10 (2.07), S, 4.80 (4.85).

Example 3. Synthesis of 1-(2-hydroxyethyl)-1-methylpyrrolidinium chloride

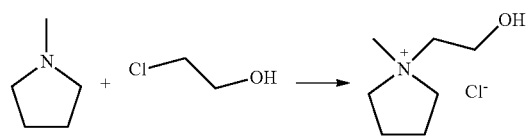

14.8 g (174 mmol) of methylpyrrolidine are heated in 20 ml of chloroethanol at 70° C. for 7 hours. The clear, pale yellow solution is admixed with 25 ml of diethyl ether, causing the product to precipitate. The precipitate is isolated by filtration and washed with diethyl ether, to give 28 g of 1-(2-hydroxyethyl)-1-methylpyrrolidinium chloride in the form of a pale yellow, waxlike solid. The yield is 97%.

$^1$H NMR (solvent: CD$_3$CN), δ (ppm): 6.05 (t, J=5.7 Hz, 1H); 3.91 (m, 2H); 3.62 (m, 4H); 3.52 (m, 2H); 3.15 (s, 3H); 2.14 (m, 4H).

$^{13}$C{$^1$H} NMR (solvent: CD$_3$CN), δ (ppm): 66.6 s; 66.2 s; 56.9 s; 49.5 s; 22.3 s.

Example 4. Synthesis of 1-methyl-1-(2-((methylsulfonyl)oxy)ethyl)-pyrrolidinium chloride

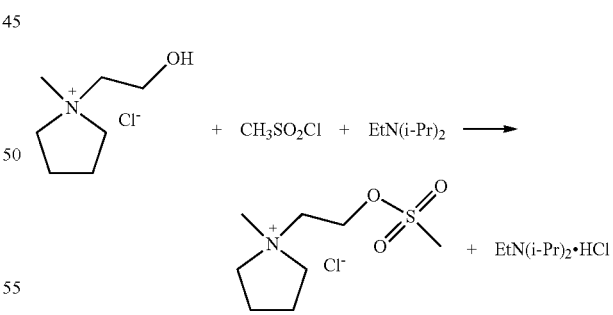

5.3 g (32 mmol) of 1-(2-hydroxyethyl)-1-methylpyrrolidinium chloride are taken up in 25 ml of dichloromethane and admixed with 4.6 g (35.7 mmol) of diisopropyl ethylamine. Subsequently 5 g (43 mmol) of methanesulfonyl chloride are added slowly dropwise, with cooling in an ice bath, the temperature being held below 15° C. The product is precipitated in the form of a colorless solid and after a reaction time of four hours is isolated by filtration. This gives 5.2 g of 1-methyl-1-(2-(methylsulfoxy)ethyl)pyrrolidinium chloride. The yield is 66%.

¹H NMR (solvent: DMSO-D₆), δ (ppm): 4.75 (m, 2H); 3.94 (m, 2H); 3.61 (m, 4H); 3.38 (s, 3H); 3.13 (s, 3H); 2.09 (m, 4H).

¹³C{¹H} NMR (solvent: DMSO-D₆), δ (ppm): 64.9 s; 64.6 s; 61.7 s; 48.2 s; 37.7 s; 21.3 s.

Example 5. Synthesis of 1-methyl-1-(2-((methylsulfonyl)oxy)ethyl)-pyrrolidinium tris(pentafluoroethyl)trifluorophosphate

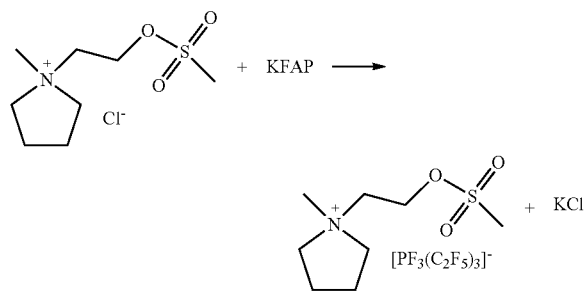

5.2 g (21 mmol) of 1-methyl-1-(2-(methylsulfoxy)ethyl) pyrrolidinium chloride are dissolved in 20 ml of ice-cold water, and 9.7 g (20 mmol) of KFAP are added in the form of an aqueous solution. The resulting precipitate is isolated by filtration, washed with five times 30 ml of ice-cold water, and dried in a desiccator. This gives 12.6 g of 1-methyl-1-(2-(methylsulfonyloxy)ethyl)-pyrrolidinium tris(pentafluoroethyl)trifluorophosphate in the form of a pale pink solid. The yield is 96%.

¹H NMR (solvent: CD₃CN), δ (ppm): 4.59 (m, 2H); 3.68 (m, 2H); 3.52 (m, 4H); 3.13 (s, 3H); 3.03 (s, 3H); 2.19 (m, 4H).

¹³C{¹H} NMR (cation) (solvent: CD₃CN), δ (ppm): 66.9 s; 64.7 s; 63.8 s; 50.0 s; 38.3 s; 22.4 s.

Example 6. Synthesis of 1-methyl-1-(2-((methylsulfonyl)oxy)ethyl)-pyrrolidinium-bis(oxalatoborate)

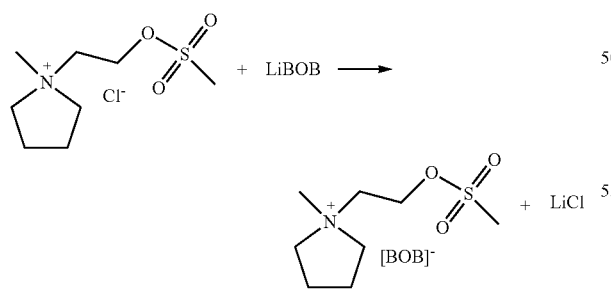

The synthesis takes place in the same way as for Example 5, by reaction with lithium bis(oxalato)borate. Yield is 86%.

¹H NMR (solvent: DMSO-D₆), δ (ppm): 4.68 (m, 2H); 3.81 (m, 2H); 3.54 (m, 4H); 3.31 (s, 3H); 3.06 (s, 3H); 2.11 (m, 4H).

¹¹B NMR (solvent: DMSO-d₆) δ (ppm): 7.4 (s),

Example 7. Alternative Synthesis of 3-(1-methylpyrrolidinium-1-yl)propane-1-sulfonate

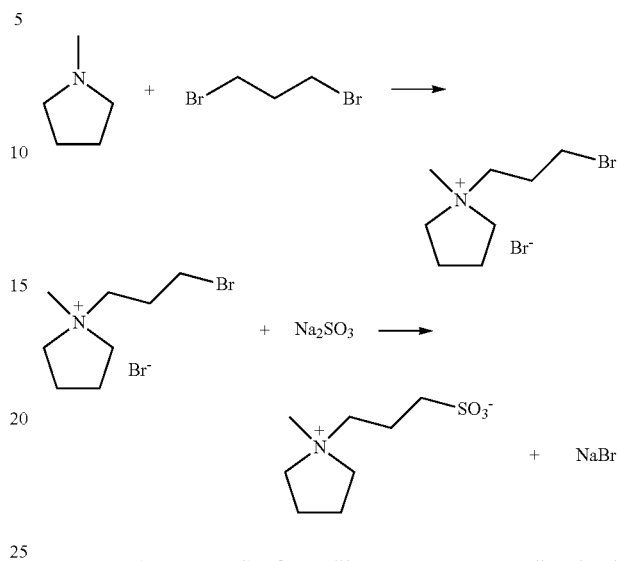

16.1 g (79.6 mmol) of 1,3-dibromopropane are dissolved in 25 ml of THF, and 6.0 g (70.6 mmol) of methylpyrrolidine are added. As early as toward the end of the addition, a finely divided, colorless precipitate is formed. The mixture is stirred at room temperature for 25 hours and the colorless precipitate is isolated by filtration. This gives 17.2 g of 1-(3-bromopropyl)-1-methylpyrrolidinium bromide in the form of a colorless, hygroscopic solid. Yield 85%.

¹H NMR (solvent: CD₃CN), δ (ppm): 3.59 (m, 8H), 3.09 (s, 3H), 2.35 (m, 2H), 2.16 (m, 4H).

¹³C{¹H} NMR (solvent: CD₃CN), δ (ppm): 65.8, 63.6, 49.7, 30.9, 28.2, 22.7.

An aqueous solution of 1-(3-bromopropyl)-1-methylpyrrolidinium bromide (1.9 g; 6.5 mmol) is admixed with 1.0 g of sodium sulfite (8.3 mmol) and heated at 85° C. for three hours. The solvent is removed under reduced pressure, to give 3-(1-methylpyrrolidinium)propane-1-sulfonate in the form of a colorless solid. The conversion is quantitative.

NMR corresponds to the product from the reaction of methylpyrrolidine with 1,3-propane sultone (Example 1).

Example 8. Synthesis of 1-(bromomethyl)-1-methylpyrrolidinium bromide

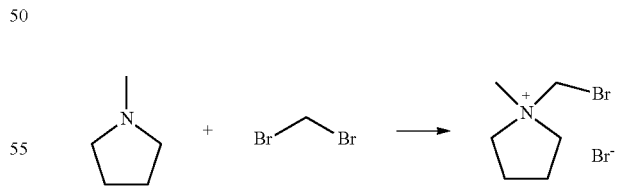

21.5 g (123.7 mmol) of dibromomethane are dissolved in 20 ml of THF, and 9.6 g (112.7 mmol) of methylpyrrolidine are added. As early as toward the end of the addition, a finely divided, colorless precipitate is formed. The mixture is stirred at room temperature for 16 hours and the colorless precipitate is isolated by filtration and washed with THF. This gives 4.8 g of 1-(bromomethyl)-1-methylpyrrolidinium bromide in the form of a colorless, hygroscopic solid. Yield 16%.

The yield is increased by longer reaction time. From a solution at rest, the product is obtained in the form of fine needles.

$^1$H NMR (solvent: DMSO-D$_6$), δ (ppm): 5.56 (s, 2H), 3.68 (m, 4H), 3.21 (s, 3H), 2.15 (m, 4H). $^{13}$C{$^1$H} NMR (solvent: DMSO-D$_6$), δ (ppm): 63.9 s, 57.4 s, 48.7 s, 21.8 s.

Electrochemical Characterization:

Test Setup

The test cells used are lithium ion cells consisting of a graphite electrode, a polyolefin-based separator, and an LiNiMnCoO$_2$ electrode (electrode area 25 cm$^2$ each, pouch cell construction). Prior to the building of the test cells, both electrodes are dried at 120° C. under reduced pressure, and the separator at 50° C. without reduced pressure, for at least 24 hours.

Test Cell Building:

The anode is placed centrally onto the laminated aluminum foil, so that the current collector protrudes about 20 mm beyond the foil.

The cathode is placed onto the anode in such a way that the anode forms a uniform frame around the cathode.

A second laminated aluminum foil is placed such that the two foils lie congruently over one another. In order to avoid short circuits, a PE film is placed in each case between current collector and laminated aluminum foil.

At the top edge, a weld seam is put in place with welding tongs (temperature 225° C.), so that the electrode stack can no longer slip.

Under an inert gas atmosphere of argon, both electrodes are wetted with 1 ml each of the test electrolyte, and a polyolefin separator, placed beforehand for 5 minutes in a Petri dish filled with electrolyte, is placed between anode and cathode.

The left-hand and right-hand sides of the test cell are welded shut with welding tongs (225° C.). Using the vacuum welding apparatus, the test cell is evacuated and sealed.

Voltage and resistance of the test cell are checked with a commercial multimeter, and are between −0.200 to 0.200 V and between 0.05 and 1 Ohm, respectively. Cells which lie outside of the values are not used.

Measurement Program

All test cells are cycled between 3.0 V and 4.2 V at 25° C. The current rates used in this case are as follows:

Phase 1:
Cycle 1-50: Charge rate: 0.3C Discharge rate 0.3C
Phase 2:
Cycle 51: Charge rate: 1C Discharge rate 1C
Cycle 52: Charge rate: 1C Discharge rate 2C
Cycle 53: Charge rate: 1C Discharge rate 4C
Cycle 54: Charge rate: 1C Discharge rate 6C
Cycle 55: Charge rate: 1C Discharge rate 8C
Cycle 56: Charge rate: 1C Discharge rate 10C
Phase 3:
Cycle 57-107: Charge rate: 1C Discharge rate 1C
Further phases: As for phases 2 and 3
The following parameters are recorded per cycle:
Charge capacity and discharge capacity in mAh
Internal resistance in the charged state (4.2V)
Internal resistance in the uncharged state (3V)

The measuring instrument/cycler used is a commercial device from the company BaSyTec.

Example A: Reference/Comparative System

The abovementioned test setup is produced with the electrolyte system 1M LiPF$_6$ in EC:DMC (1:1) (EC=ethylene carbonate, DMC—dimethyl carbonate).

The durability (1C-10C—The discharge capacity at 1C is taken as 100%) is shown by FIG. 1.

The tables below show the results:

Table 1 shows the results of the loading test:

| C rate | 1 C | 2 C | 4 C | 6 C | 8 C | 10 C |
|---|---|---|---|---|---|---|
| Relative discharge capacity | 100% | 96% | 85% | 64% | 48% | 35% |

FIG. 2 shows the profile of the internal resistance in the uncharged state (3.0V).

Table 2 is a summary of the cycling test (the discharge capacity in the 10th cycle is taken as 100%)

| Cycle | 50 | 100 | 200 | 300 | 400 | 500 | |
|---|---|---|---|---|---|---|---|
| Rel. discharge capacity | 99 | 94 | 93 | 93 | 92 | 91 | % |
| Internal resistance at 3.0 V | 0.9 | 1.0 | 1.1 | 1.3 | 1.4 | 1.6 | Ohms |
| Internal resistance at 4.2 V | 3.7 | 3.6 | 3.8 | 4.2 | 4.7 | 4.9 | Ohms |

Table 3 is a summary of the relative discharge capacity at 10C (the discharge capacity of the 1st 1C discharging is taken as 100%)

| | Number of repetition of the loading test | | | | | | |
|---|---|---|---|---|---|---|---|
| | 1 | 2 | 3 | 4 | 5 | 6 | 7 |
| Relative discharge capacity at 10 C | 35 | 30 | 30 | 25 | 25 | 23 | 20 % |

In summary, for the first loading with 10C, a derivable capacity of just 35% is found (FIG. 1). This falls with increasing repetition of the load. In the case of the 7th run (about 500th cycle, FIG. 2) a derivable capacity of only about 20% is measured. Even after the first strong loading of 10C, the cell does not achieve the capacity figures measured beforehand (FIG. 2). At the same time it is notable that the internal resistance in the charged state rises slightly over the number of cycles (FIG. 3), and rises sharply in the uncharged state (FIG. 4).

Example B: Electrolyte comprising 1-(3-(methoxysulfonyl)propyl)-1-methylpyrrolidinium tris(pentafluoroethyl)trifluorophosphate The above test setup is implemented with the electrolyte system 1M LiPF$_6$ in EC:DMC (1:1)+1% 1-(3-(methoxysulfonyl)propyl)-1-methylpyrrolidinium-tris(pentafluoroethyl)trifluorophosphate.

FIGS. 3 and 4 and also Tables 4 to 6 show the results.

FIG. 3 shows the 1C to 10C durability: the discharge capacity at 10 is taken as 100%.

Table 4 shows the results of the loading test:

| C rate | 1 C | 2 C | 4 C | 6 C | 8 C | 10 C |
|---|---|---|---|---|---|---|
| Relative discharge capacity | 100% | 97% | 89% | 70% | 48% | 32% |

The profile of the internal resistance in the uncharged state (3V) is shown by FIG. 4.

Table 5 provides a summary of the cycling test (the discharge capacity in the 10th cycle is taken as 100%).

| Cycle | 50 | 100 | 200 | 300 | 400 | |
|---|---|---|---|---|---|---|
| Rel. discharge capacity | 100 | 98 | 98 | 99 | 98 | % |
| Internal resistance at 3 V | 0.94 | 0.95 | 0.99 | 1.02 | 1.05 | Ohms |
| Internal resistance at 4.2 V | 2.07 | 2.14 | 1.99 | 2.02 | 2.14 | Ohms |

Table 6 gives a summary of the relative discharge capacity at 10C (the discharge capacity of the 1st 1C discharge is taken as 100%).

| | Number of repetition of the loading test | | | | | | | |
|---|---|---|---|---|---|---|---|---|
| | 1 | 2 | 3 | 4 | 5 | 6 | 7 | |
| Relative discharge capacity at 10 C | 32 | 25 | 28 | 25 | 27 | 26 | 25 | % |

In summary, for the first loading with 10C, a derivable capacity of 32% is found (FIG. 5). In contrast to the situation with the reference, the drop is significantly less with increasing repetition of the loading, and even after the 7th run (400 cycles) it still achieves 25%. Under the same conditions, the reference falls to 20%.

In contrast to the situation in the reference cell (Example A), the capacity measured in the first cycles is regained even after multiple loading with 10C. The cell ages much more slowly and exhibits amazingly low capacity fading.

Striking at the same time is the very constant profile of the internal resistances. In the discharged state in particular, the internal resistance remains very constant over 400 cycles, and shows a reduction by a factor of 2 in comparison to the reference.

Example C: Electrolyte comprising 1-methyl-1-(2-(methylsulfoxy)ethyl)-pyrrolidinium tris(pentafluoroethyl)trifluorophosphate The above test setup is implemented with the electrolyte system 1M $LiPF_6$ in EC:DMC (1:1)+1% 1-methyl-1-(2-(methylsulfoxy)ethyl)-pyrrolidinium tris(pentafluoroethyl)trifluorophosphate.

FIGS. 5 and 6 and also Tables 7 to 9 show the results.

FIG. 5 shows the 1C to 10C durability: the discharge capacity at 1C is taken as 100%.

Table 7 shows the results of the loading test:

| C rate | 1 C | 2 C | 4 C | 6 C | 8 C | 10 C |
|---|---|---|---|---|---|---|
| Relative discharge capacity | 100% | 98% | 90% | 71% | 54% | 43% |

The profile of the internal resistance in the uncharged state (3.0V) is shown by FIG. 6.

Table 8 provides a summary of the cycling test (the discharge capacity in the 10th cycle is taken as 100%).

| Cycle | 50 | 100 | 200 | 300 | 400 | |
|---|---|---|---|---|---|---|
| Rel. discharge capacity | 100 | 98 | 96 | 95 | 95 | % |
| Internal resistance at 3.0 V | 0.9 | 0.9 | 1.0 | 1.0 | 1.1 | Ohms |
| Internal resistance at 4.2 V | 3.6 | 2.1 | 2.2 | 2.3 | 2.3 | Ohms |

Table 9 gives a summary of the relative discharge capacity at 10C (the discharge capacity of the 1st 1C discharge is taken as 100%).

| Number of repetition of the loading test | 1 | 2 | 3 | 4 | 5 | 6 | |
|---|---|---|---|---|---|---|---|
| Relative discharge capacity at 10 C | 43 | 42 | 39 | 39 | 35 | 36 | % |

In summary, in the first loading with 10C, a derivable capacity is found which is much higher in comparison to the reference, of 43% (FIG. 5).

At the same time, as for example B, the very constant profile of the internal resistances is striking. In particular in the discharged state, as with example B, the internal resistance is situated at very low values, and well below the reference (reduction by a factor of 2).

With this additive as well, a significantly lower ageing and capacity fading is achieved.

Example D: Electrolyte comprising 1-methyl-1-(2-(methylsulfoxy)ethyl)-pyrrolidinium-bis(oxalato)borate The above test setup is implemented with the electrolyte system 1M $LiPF_6$ in EC:DMC (1:1)+1% 1-methyl-1-(2-(methylsulfoxy)ethyl)-pyrrolidinium-bis(oxalato)borate.

FIGS. 7 and 8 and also Tables 10 to 12 show the results.

FIG. 7 shows the 1C to 10C durability: the discharge capacity at 1C is taken as 100%.

Table 10 shows the results of the loading test:

| C rate | 1 C | 2 C | 4 C | 6 C | 8 C | 10 C |
|---|---|---|---|---|---|---|
| Relative discharge capacity | 100% | 98% | 85% | 68% | 52% | 40% |

The profile of the internal resistance in the uncharged state (3.0V) is shown by FIG. 8.

Table 11 provides a summary of the cycling test (the discharge capacity in the 10th cycle is taken as 100%).

| Cycle | 50 | 100 | 200 | 300 | 400 | |
|---|---|---|---|---|---|---|
| Rel. discharge capacity | 98 | 97 | 96 | 96 | | % |
| Internal resistance at 3.0 V | 0.99 | 0.98 | 0.99 | | 0.99 | Ohms |
| Internal resistance at 4.2 V | 2.2 | 2.1 | 2.0 | | 2.0 | Ohms |

Table 12 shows the summary of the relative discharge capacity at 10C (the discharge capacity of the 1st 1C discharge is taken as 100%).

| Number of repetition of the loading test | 1 | 2 | 3 | 4 | |
|---|---|---|---|---|---|
| Relative discharge capacity at 10 C | 40 | 39 | 39 | 38 | % |

Similarly to the situation in examples B and C, for the loading with 10C, a derivable capacity is found which is much higher in comparison to the reference, of 40%. At the same time, as for example B and C, the very constant profile of the internal resistances is striking. The internal resistance particularly in the discharged state is well below the reference.

INDEX TO THE FIGURES

Figure 1:
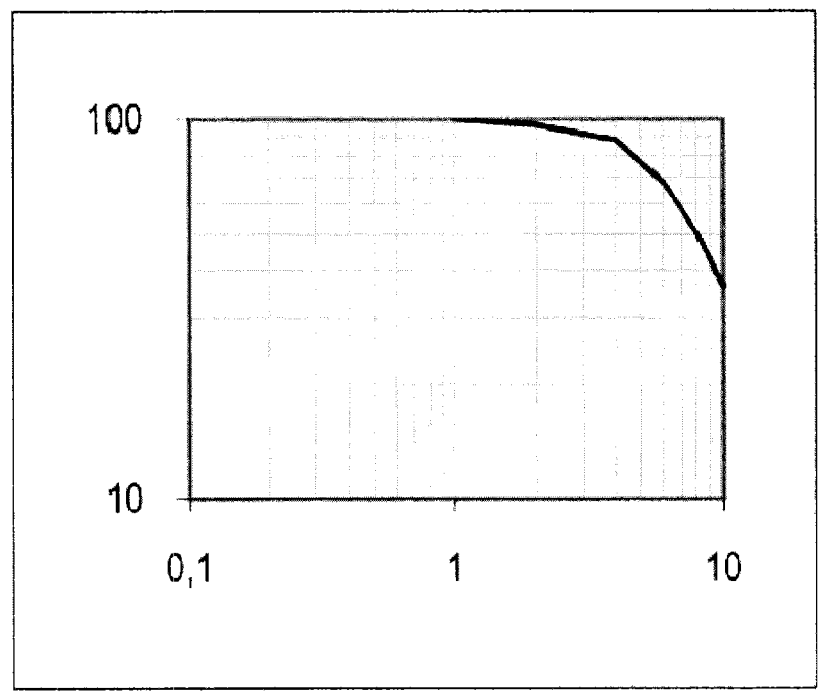
FIG. 1 shows the 1C to 10C durability of the reference system 1M $LiPF_6$ in EC:DMC (1:1).
Figure 2:
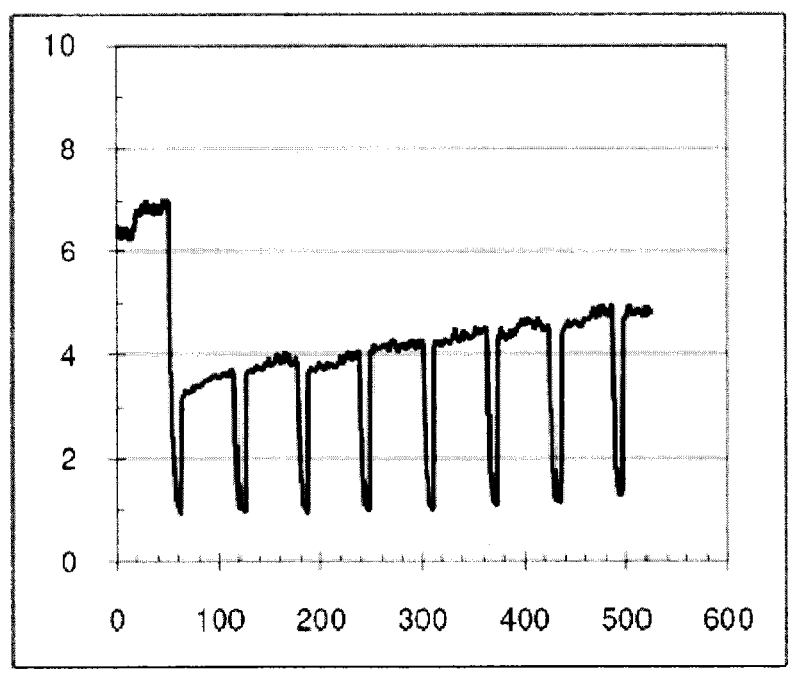
FIG. 2 shows the profile of the internal resistance in the uncharged state (3.0V) of the reference system 1M $LiPF_6$ in EC:DMC (1:1).
Figure 3:
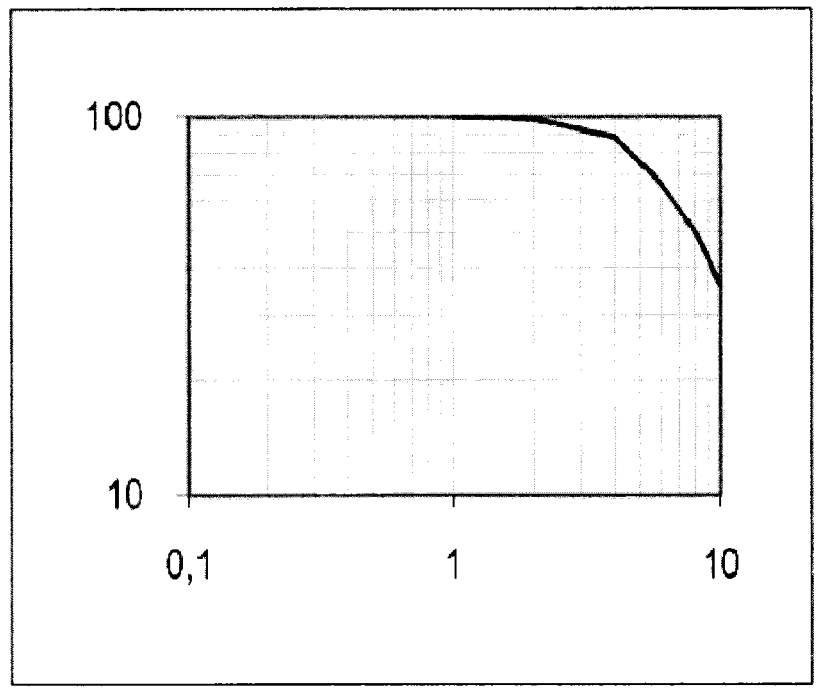
FIG. 3 shows the 1C to 10C durability of example B 1M LiPF$_6$ in EC:DMC (1:1), 1% 1-(3-(methoxysulfonyl)propyl)-1-methylpyrrolidinium tris(pentafluoroethyl)trifluorophosphate.
Figure 4:
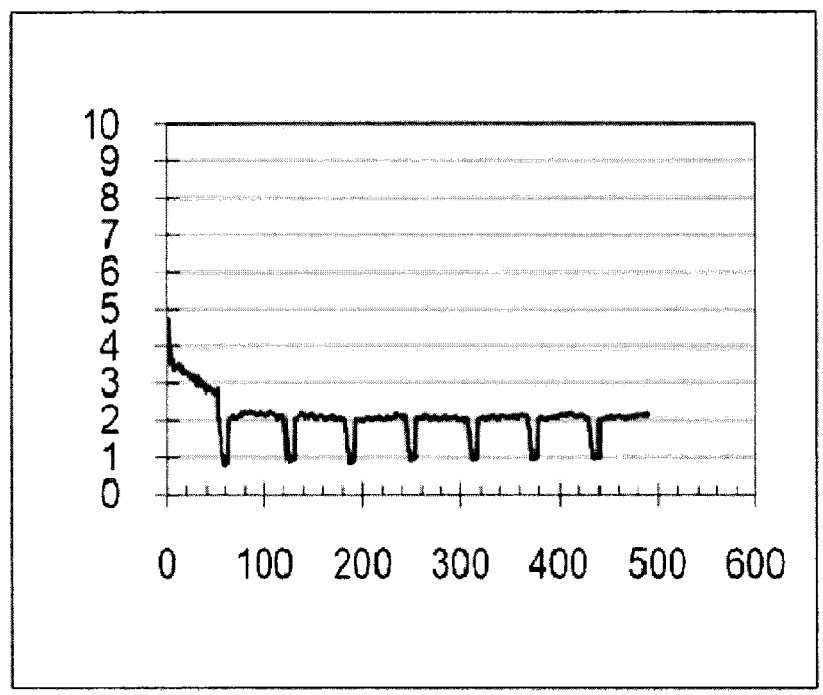
FIG. 4 shows the profile of the internal resistance in the uncharged state (3.0V) of the example B 1M LiPF$_6$ in EC:DMC (1:1), 1% 1-(3-(methoxysulfonyl)propyl)-1-methylpyrrolidinium-tris(pentafluoroethyl)trifluorophosphate.
Figure 5:
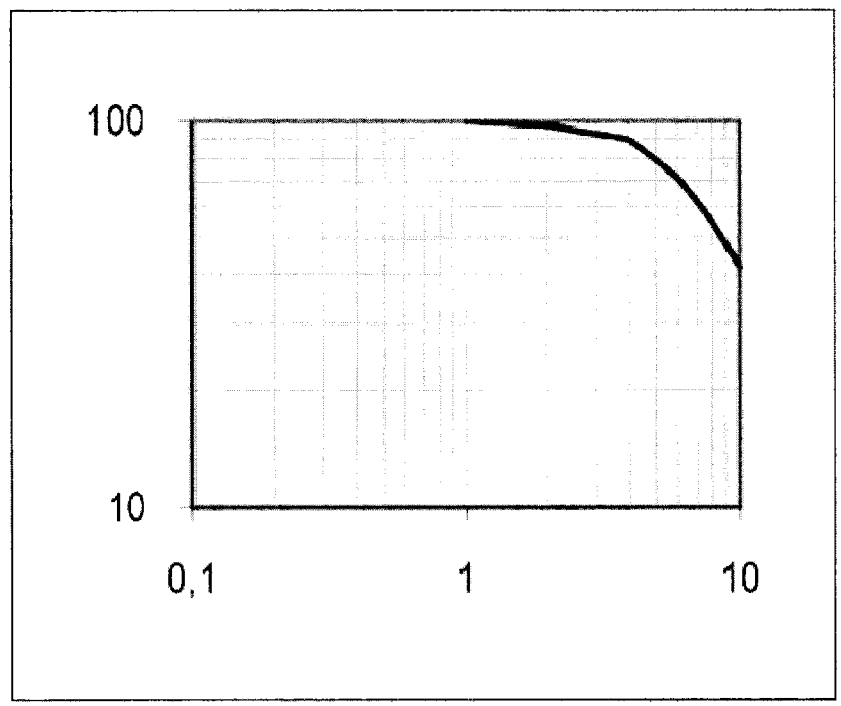
FIG. 5 shows the 1C to 10C durability of example C 1M LiPF$_6$ in EC:DMC (1:1), 1% 1-methyl-1-(2-(methylsulfoxy)ethyl)pyrrolidinium tris(pentafluoroethyl)trifluorophosphate.
Figure 6:
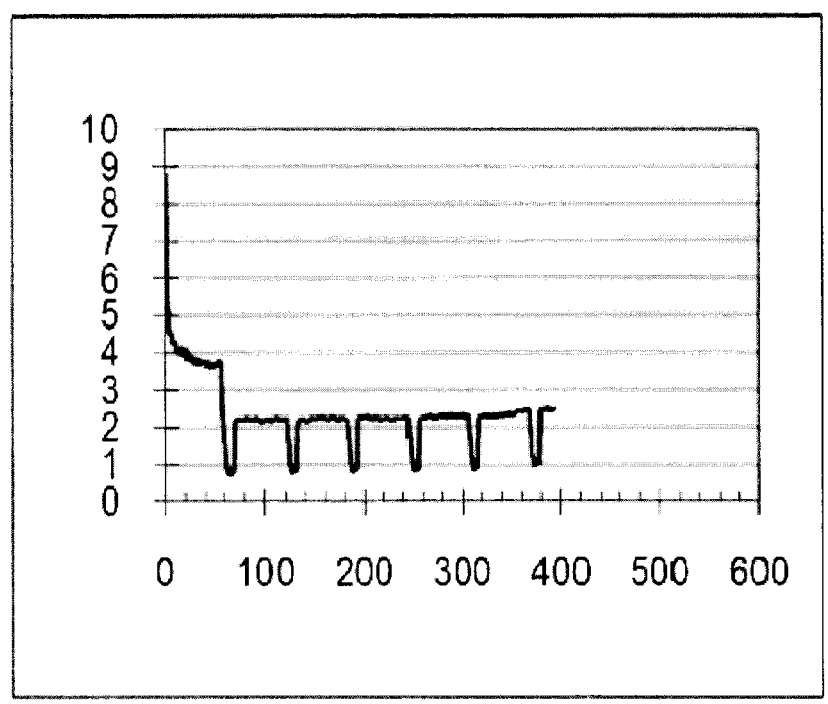
FIG. 6 shows the profile of the internal resistance in the uncharged state (3.0V) of the example C 1M LiPF$_6$ in EC:DMC (1:1), 1% 1-methyl-1-(2-(methylsulfoxy)ethyl)-pyrrolidinium-tris(pentafluoroethyl)trifluorophosphate.
Figure 7:
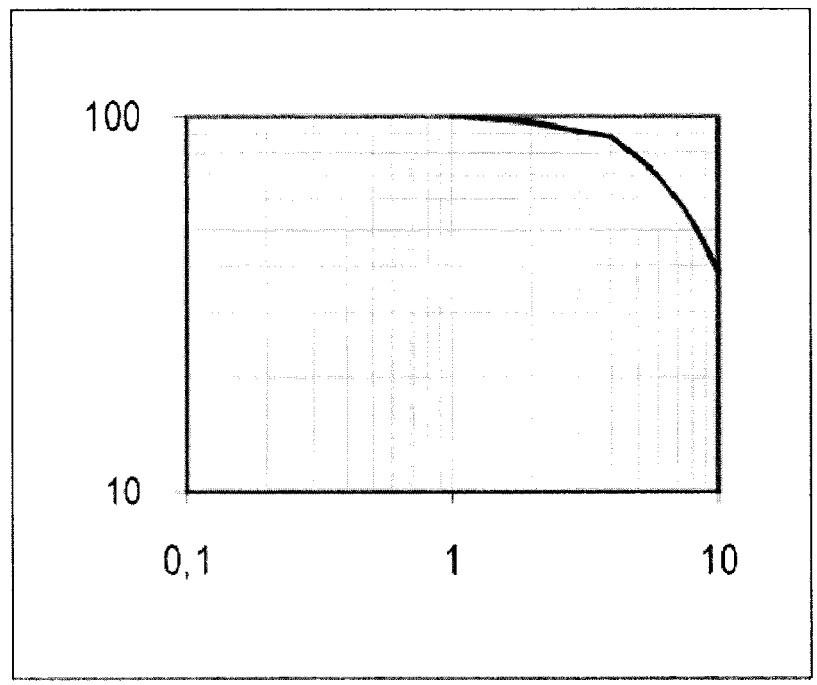
FIG. 7 shows the 1C to 10C durability of example D 1M LiPF$_6$ in EC:DMC (1:1), 1% 1-methyl-1-(2-(methylsulfoxy)ethyl)pyrrolidinium bis(oxalato)borate.
Figure 8:
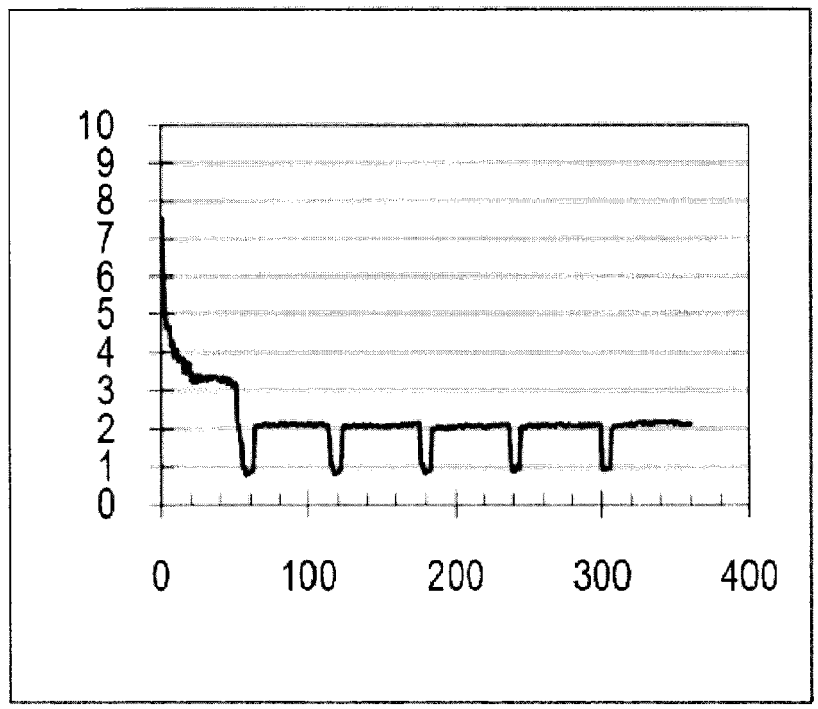
FIG. 8 shows the profile of the internal resistance in the uncharged state (3.0V) of the example D 1M LiPF$_6$ in EC:DMC (1:1), 1% 1-methyl-1-(2-(methylsulfoxy)ethyl) pyrrolidinium bis(oxalato)borate.

The invention claimed is:

1. An electrolyte additive comprising a compound of formula I

[K—(CH$_2$)—(CH$_2$)$_u$—SO$_3$—(CH$_2$)$_v$—R"]$^+$[A]$^-$    I, wherein u is 0, 1, 2, 3, 4, 5, 6 or 7 and where a CH$_2$ group of the —(CH$_2$)$_u$-alkylene chain may be replaced by O or may have a double bond, v is 0, 1, 2, 3 or 4, —SO$_3$— is

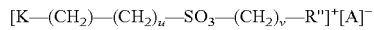

R" independently at each occurrence is a straight-chain or branched alkyl group having 1 to 20 C atoms, and may be unfluorinated, partly fluorinated or fully fluorinated, or is a straight-chain or branched alkenyl group having 2 to 20 C atoms and a double bond, a straight-chain or branched alkynyl group having 2 to 20 C atoms and a triple bond, or an aryl group having 6 to 12 C atoms, which group may be singly or multiply substituted by at least one selected from the group consisting of F, Cl, and a straight-chain or branched, partly fluorinated or fully fluorinated alkyl group having 1 to 8 C atoms, K is a cation selected from the group consisting of R$_3$N$^+$—*, R$_3$P$^+$—*,

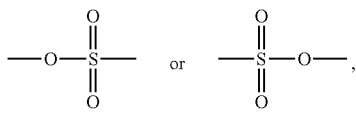

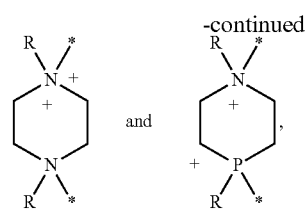

wherein

R independently at each occurrence is methyl, ethyl, n-propyl, isopropyl, n-butyl, sec-butyl or tert-butyl, wherein optionally a CH$_2$ group, not directly joined to N or P, in the radicals R is replaced by O, Y is CH$_2$, O, S or NR', R' is methyl, ethyl, n-propyl, isopropyl, n-butyl, sec-butyl or tert-butyl, A is an anion selected from the group consisting of

[F$_z$B(C$_m$F$_{2m+1}$)$_{4-z}$]$^-$,
[F$_y$P(C$_m$F$_{2m+1}$)$_{6-y}$]$^-$,
[(C$_m$F$_{2m+1}$)$_2$P(O)O]$^-$,
[C$_m$F$_{2m+1}$P(O)O$_2$]$^{2-}$,
[O—C(O)—C$_m$F$_{2m+1}$]$^-$,
[N(C(O)—C$_m$F$_{2m+1}$)$_2$]$^-$,
[N(S(O)$_2$—C$_m$F$_{2m+1}$)$_2$]$^-$,
[N(C(O)—C$_m$F$_{2m+1}$)(S(O)$_2$—C$_m$F$_{2m+1}$)]$^-$,
[N(C(O)—C$_m$F$_{2m+1}$)(C(O)F)]$^-$,
[N(S(O)$_2$—C$_m$F$_{2m+1}$)(S(O)$_2$F)]$^-$,
[N(S(O)$_2$F)$_2$]$^-$,
[C(C(O)—C$_m$F$_{2m+1}$)$_3$]$^-$,
[C(S(O)$_2$—C$_m$F$_{2m+1}$)$_3$]$^-$,
[O—S(O)$_2$—C$_m$F$_{2m+1}$]$^-$,

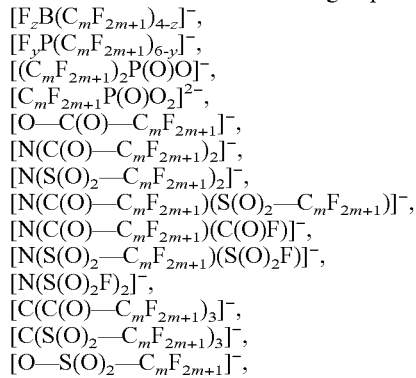

m is 1, 2, 3, 4, 5, 6, 7 or 8, wherein optionally CF$_2$ groups in the anions are replaced by O, S(O)$_2$, NR or CH$_2$, z is 1,2 or 3, y is 1, 2, 3, 4, 5 or 6, X is B or Al, R$^1$ and R$^2$ are each independently of one another F, Cl, Br, I, a straight-chain or branched perfluoroalkyl group having 1 to 20 C atoms, a straight-chain or branched alkoxy group having 1 to 20 C atoms, which may be unfluorinated, partly fluorinated or fully fluorinated, or —O—C(O)— alkyl, where alkyl is a straight-chain or branched alkyl group having 1 to 20 C atoms, and may be unfluorinated, partly fluorinated or perfluorinated, and where

independently at each occurrence is a bidentate radical which derives from a 1,2- or 1,3-diol, from a 1,2- or 1,3-dicarboxylic acid or from a 1,2- or 1,3-hydroxycarboxylic acid, by entering of pairs of adjacent OH groups in the compound into one bond each to the central atom X, accompanied by formal elimination of two H atoms, wherein an electroneutrality of a corresponding salt thereof is observed.

2. The electrolyte additive according to claim 1, wherein v is 0.

3. The electrolyte additive according to claim 1, wherein u is 1, 2 or 3.

4. The electrolyte additive according to claim 1, wherein R" is a straight-chain or branched alkyl group having 1 to 8 C atoms, and may be unfluorinated, partly fluorinated or fully fluorinated.

5. The electrolyte additive according to claim 1, wherein K is cation

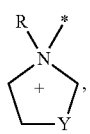

and where [A]⁻ is selected from the group consisting of [O—S(O)$_2$—C$_m$F$_{2m+1}$]⁻ and [F$_z$B(C$_m$F$_{2m+1}$)$_{4-z}$], wherein z=4.

6. The electrolyte additive according to claim 1, wherein A is an anion selected from the group consisting of
[F$_z$B(C$_m$F$_{2m+1}$)$_{4-z}$]⁻,
[F$_y$P(C$_m$F$_{2m+1}$)$_{6-y}$]⁻,
[O—C(O)—C$_m$F$_{2m+1}$]⁻,
[N(S(O)$_2$—C$_m$F$_{2m+1}$)$_2$]⁻,
[N(S(O)$_2$F)$_2$]⁻,

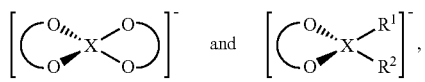

wherein
m is 1, 2, 3, 4, 5, 6, 7 or 8,
z is 1, 2 or 3,
y is 3, 4, 5 or 6,
X is B,
R¹ and R² are each independently of one another F, a straight-chain or branched perfluoroalkyl group having 1 to 4 C atoms, a straight-chain or branched alkoxy group having 1 to 4 C atoms or —O—C(O)-alkyl, where alkyl is a straight-chain or branched alkyl group having 1 to 20 C atoms, and may be unfluorinated, partly fluorinated or perfluorinated,
and
where

independently at each occurrence is a bidentate radical which derives from a 1,2- or 1,3-diol, from a 1,2- or 1,3-dicarboxylic acid or from a 1,2- or 1,3-hydroxycarboxylic acid, by entering of pairs of adjacent OH groups in the compound into one bond each to the central atom X, accompanied by formal elimination of two H atoms.

7. A process for preparing a compound of formula I according to claim 1, wherein SO$_3$ is substructure

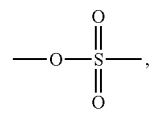

the process comprising reacting a compound of formula (II)

K-1                                                            (II), wherein K-1 is selected from the group consisting of R$_3$N, R$_3$P,

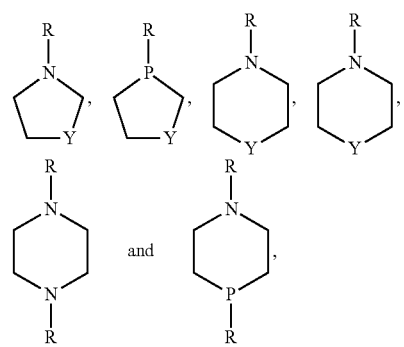

R independently at each occurrence is methyl, ethyl, n-propyl, isopropyl, n-butyl, sec-butyl or tert-butyl, and a CH$_2$ group, not joined to N or P, in the radicals R may be replaced by O,
Y is CH$_2$, O, S or NR', and
R' is methyl, ethyl, n-propyl, isopropyl, n-butyl, sec-butyl or tert-butyl,
with a compound of formula (III), Hal-(CH$_2$)—(CH$_2$)$_u$—OH                      (III), wherein u is 1, 2, 3, 4, 5, 6 or 7, and a CH$_2$ group, not attached to the oxygen, in the —(CH$_2$)$_u$-alkylene chain may be replaced by O or may contain a double bond, and Hal is Cl, Br or I,
to obtain a resultant intermediate compound of the formula (IV)

[K—(CH$_2$)—(CH$_2$)$_u$—OH]⁺[Hal]⁻             (IV), reacting the resultant intermediate compound of formula (IV) with a compound of formula (V)

R"—(CH$_2$)$_v$—SO$_2$-L                            (V), wherein L is a leaving group selected from a straight-chain or branched alkoxy group having 1 to 3 C atoms, Cl or F,
with acid catalysis in the case of the alkoxy group as leaving group, or in the presence of a base in the case of Cl or F as leaving group, to obtain a resulting compound of formula (VI)

[K—(CH$_2$)—(CH$_2$)$_u$—SO$_3$—(CH$_2$)$_v$—R"]⁺[Hal]⁻     (VI), and then reacting the resulting compound of formula (VI) in a metathesis reaction with a compound of formula (VII),

[Kt]⁺[A]⁻                                                           (VII), wherein [Kt]⁺ is an alkali metal cation or H⁺, and [A]⁻ has a definition indicated in claim 1.

8. A process for preparing a compound of formula I according to claim 1, wherein SO$_3$ is substructure

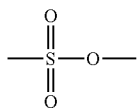

and u is 2, 3, 4 or 5, the process comprising reacting a compound of formula (II)

K-1 (II), wherein K-1 is selected from the group $R_3N$, $R_3P$,

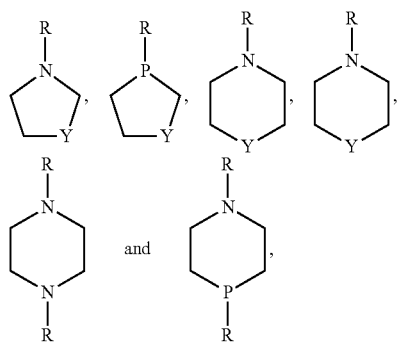

R independently at each occurrence is methyl, ethyl, n-propyl, isopropyl, n-butyl, sec-butyl or tert-butyl, and a $CH_2$ group, not joined to N or P, in the radicals R may be replaced by O, Y is $CH_2$, O, S or NR', and R' is methyl, ethyl, n-propyl, isopropyl, n-butyl, sec-butyl or tert-butyl, with a compound of formula (VIII)

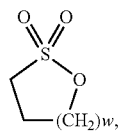 VIII wherein w is 1, 2, 3 or 4,
to obtain an intermediate compound of formula (IX)

[K—(CH$_2$)—(CH$_2$)$_u$—SO$_3^-$] (IX), subsequently reacting the intermediate compound of formula (IX) with an alkylating agent of formula (X)

L*-(CH$_2$)$_v$—R" (X), wherein L* is $CF_3$—S(O)$_2$O, $C_4F_9$—S(O)$_2$O, $(C_2F_5)_2$P(O)O, $(C_4F_9)_2$P(O)O, (alkyl)$_2$O$^+$, alkyl-S(O)$_2$O, alkyl-O—S(O)$_2$O, I or Br, with alkyl independently at each occurrence being a straight-chain or branched alkyl group having 1 to 4 C atoms, to obtain a resulting compound of formula (XI)

[K—(CH$_2$)—(CH$_2$)$_u$—SO$_3$—(CH$_2$)$_v$—R"]$^+$[L*]$^-$ (XI), and then optionally reacting the resulting compound of formula (XI) with a compound of formula (VII),

[Kt]$^+$[A]$^-$ (VII), wherein [Kt]$^+$ is an alkali metal cation or H$^+$, and [A]$^-$ has a definition stated in claim 1.

9. A process for preparing a compound of formula I according to claim 1, where SO$_3$ is substructure

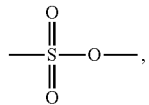

the process comprising reacting a compound of formula (II)

K-1 (II), wherein K-1 is selected from the group consisting of $R_3N$, $R_3P$,

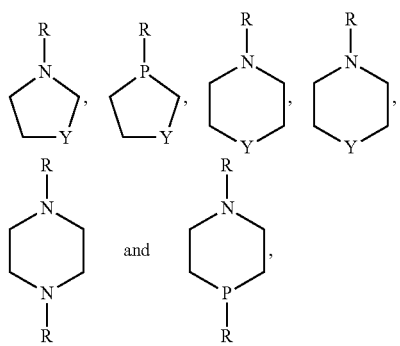

R independently at each occurrence is methyl, ethyl, n-propyl, isopropyl, n-butyl, sec-butyl or tert-butyl, and at least one $CH_2$ group, not joined to N or P, in the radicals R may be replaced by O, Y is $CH_2$, O, S or NR', and R' is methyl, ethyl, n-propyl, isopropyl, n-butyl, sec-butyl or tert-butyl, with a compound of formula (XII), Hal-(CH$_2$)—(CH$_2$)$_u$-Hal (XII), wherein u is 0, 1, 2, 3, 4, 5, 6 or 7, and a $CH_2$ group, not attached to Hal, in the —(CH$_2$)$_u$-alkylene chain may be replaced by O or may contain a double bond, and Hal is Cl, Br or I, to obtain a resultant intermediate compound of formula (XIII)

[K—(CH$_2$)—(CH$_2$)$_u$—Hal]$^+$[Hal]$^-$ (XIII), reacting the resultant intermediate compound of formula (XIII) with an alkali metal sulfite or ammonium sulfite and subsequently with a compound of formula (X)

L*-(CH$_2$)$_v$—R" (X), wherein L* is $CF_3$—S(O)$_2$O, $C_4F_9$—S(O)$_2$O, $(C_2F_5)_2$P(O)O, $(C_4F_9)_2$P(O)O, (alkyl)$_2$O$^+$, alkyl-S(O)$_2$O, alkyl-O—S(O)$_2$O, I or Br, with alkyl independently at each occurrence being a straight-chain or branched alkyl group having 1 to 4 C atoms, to obtain a resulting compound of formula (XI)

[K—(CH$_2$)—(CH$_2$)$_u$—SO$_3$—(CH$_2$)$_v$—R"]$^+$[L*]$^-$ (XI), and then optionally reacting the resulting compound of formula (XI) with a compound of formula (VII),

[Kt]$^+$[A]$^-$ (VII), wherein [Kt]$^+$ is an alkali metal cation or H$^+$, and [A]$^-$ has a definition stated in claim 1.

10. An electrolyte comprising the electrolyte additive according to claim 1, wherein $[A]^-$ is selected from the group consisting of $[O-S)O)_2^-C_mF_{2m+1}]^+$ wherein m=1, 2, 3, 4, 5, 6, 7 or 8 and $[F_zB(C_mF_{2m+1})_{4-z}]^-$ wherein z=4.

11. The electrolyte according to claim 10, further comprising as conductive salt, a lithium salt, a tetraalkylammonium salt, or both.

12. The electrolyte according to claim 10, further comprising an additional additive.

13. An electrochemical or electrooptical device, comprising the electrolyte additive according to claim 1, wherein $[A]^-$ is selected from the group consisting of $[O-S(O)_2-C_mF_{2m+1}]^-$ wherein m=1, 2, 3, 4, 5, 6, 7 or 8 and $[F_zB(C_mF_{2m+1})_{4-z}]^-$ wherein z=4.

14. The electrolyte additive according to claim 1, wherein $[A]^-$ is selected from the group consisting of $[O-S(O)_2-C_mF_{2m+1}]^-$ wherein m=1, 2, 3, 4, 5, 6, 7 or 8 and $[F_zB(C_mF_{2m+1})_{4-z}]^-$ wherein z=4.

15. An electrochemical or electrooptical device comprising the electrolyte additive according to claim 1, wherein $[A]^-$ is selected from the group consisting of $[O-S(O)_2-C_mF_{2m+1}]^-$ wherein m=1, 2, 3, 4, 5, 6, 7 or 8 and $[F_zB(C_mF_{2m+1})_{4-z}]^-$ wherein z=4.

16. The electrochemical or electrooptical device according to claim 15, wherein the electrochemical or electrooptical device is a device selected from the group consisting of a lithium battery, a lithium ion battery, a double layer capacitor, a lithium capacitor, a solar cell, an electrochromic display, a sensor and a biosensor.

\* \* \* \* \*